United States Patent
Bredt et al.

(10) Patent No.: US 12,227,771 B2
(45) Date of Patent: Feb. 18, 2025

(54) EXPRESSION SYSTEMS AND METHODS OF USE THEREOF

(71) Applicant: Janssen Pharmaceutica NV, Beerse (BE)

(72) Inventors: David S. Bredt, La Jolla, CA (US);
Weston Davini, San Diego, CA (US);
Shenyan Gu, San Diego, CA (US);
Jose Matta, San Diego, CA (US); Min Lei O'Carroll, San Diego, CA (US)

(73) Assignee: JANSSEN PHARMACEUTICA NV, Beerse (BE)

( * ) Notice: Subject to any disclaimer, the term of this patent is extended or adjusted under 35 U.S.C. 154(b) by 246 days.

(21) Appl. No.: 16/875,550

(22) Filed: May 15, 2020

(65) Prior Publication Data
US 2020/0362013 A1    Nov. 19, 2020

Related U.S. Application Data

(60) Provisional application No. 62/849,653, filed on May 17, 2019.

(51) Int. Cl.
| | |
|---|---|
| *C12N 5/00* | (2006.01) |
| *C12N 5/071* | (2010.01) |
| *C12N 9/10* | (2006.01) |
| *C07K 14/705* | (2006.01) |
| *G01N 33/50* | (2006.01) |
| *G01N 33/68* | (2006.01) |

(52) U.S. Cl.
CPC ......... *C12N 9/1029* (2013.01); *C12N 5/0602* (2013.01); *C07K 14/70571* (2013.01); *G01N 33/5008* (2013.01); *G01N 33/68* (2013.01)

(58) Field of Classification Search
CPC ............................. C12N 9/1029; C12N 5/0602
See application file for complete search history.

(56) References Cited

U.S. PATENT DOCUMENTS

| | | | | |
|---|---|---|---|---|
| 4,753,874 A * | 6/1988 | Calos | ...................... | C12Q 1/68 435/441 |
| 6,440,681 B1 | 8/2002 | Elliott et al. | | |

FOREIGN PATENT DOCUMENTS

| | | | |
|---|---|---|---|
| WO | 0119973 | A2 | 3/2001 |
| WO | 02059266 | A2 | 8/2002 |
| WO | 2004009775 | A2 | 1/2004 |
| WO | 2005030145 | A2 | 4/2005 |
| WO | 2008011006 | A2 | 1/2008 |
| WO | 2020234179 | A1 | 11/2020 |
| WO | 2022223806 | A1 | 10/2022 |
| WO | 2022223817 | A1 | 10/2022 |

OTHER PUBLICATIONS

D3DX95_HUMAN. UniProtKB/TrEMBL Database. Jul. 5, 2017.*
Naz. Mutations in a novel gene, TMIE, are associated with hearing loss linked to the DFNB6 locus. Am J Hum Genet. Sep. 2002;71(3):632-6.*
Altschul et al., "Basic Local Alignment Search Tool", J. Mol. Biol., 1990, p. 403-410, vol. 215.
Altschul et al., "Gapped BLAST and PSI-BLAST: a new generation of protein database search programs", Nucleic Acids Res., 1997, pp. 3389-3402, vol. 25, Iss 17.
Arredondo et al., "Central role of α7 nicotinic receptor in differentiation of the stratified squamous epithelium", J Cell Biol, 2002, pp. 325-336, vol. 159, Iss 2.
Elgoyhen et al., "α10: A determinant of nicotinic cholinergic receptor function in mammalian vestibular and cochlear mechanosensory hair cells", Proc Natl Acad Sci USA., 2001, pp. 3501-3506, vol. 98 Iss 6.
Elgoyhen et al., "α9: An Acetylcholine Receptor with Novel Pharmacological Properties Expressed in Rat Cochlear Hair Cells", Cell, 1994, pp. 705-715, vol. 79.
Henikoff & Henikoff, "Amino acid substitution matrices from protein blocks", Proc. Natl. Acad. Sci. USA, 1992, pp. 10915-10919, vol. 89.
Karlin & Altschul, "Applications and statistics for multiple high-scoring segments in molecular sequences", Proc. Nat'l. Acad. Sci USA, 1993, pp. 5873-5877, vol. 90.
Kumar and Meizel, "Nicotinic Acetylcholine Receptor Subunits and Associated Proteins in Human Sperm*", J Biol Chem, 2005, pp. 25928-25935, vol. 280, Iss 27.
Lansdell et al., "RIC-3 Enhances Functional Expression of Multiple Nicotinic Acetylcholine Receptor Subtypes in Mammalian Cells", Mol Pharmacol., 2005, pp. 1431-1438, vol. 68, Iss 5.
Lips et al., "Coexpression of α9 and α10 nicotinic acetylcholine receptors in rat dorsal root ganglion neurons", Neuroscience, 2002, pp. 1-5, vol. 115.
Needleman & Wunsch, "A General Method Applicable to the Search for Similarities in the Amino Acid Sequence of Two Proteins", J. Mol. Biol., 1970, pp. 443-453, vol. 48.
Pearson & Lipman, "Improved tools for biological sequence comparison", Proc. Nat'l. Acad. Sci. USA, 1988, pp. 2444-2448, vol. 85.
Peng et al., "Characterization of the human nicotinic acetylcholine receptor subunit alpha (α) 9 (CHRNA9) and alpha (α) 10 (CHRNA10) in lymphocytes", Life Sci, 2004, pp. 263-280, vol. 76.
Sgard et al., "A Novel Human Nicotinic Receptor Subunit, α10, That Confers Functionality to the α9-Subunit", Mol Pharmacol, 2002, pp. 150-159, vol. 61, Iss 1.
Smith & Waterman, "Comparison of Biosequences", Adv. Appl. Math., 1981, pp. 482-489, vol. 2.
Vincler et al., "Molecular mechanism for analgesia involving specific antagonism of α9α10 nicotinic acetylcholine receptors", Proc Natl Acad Sci USA, 2006, pp. 17880-17884, vol. 103, Iss 47.
Indurthi, et al., "Presence of multiple binding sites on α9α10 nAChR receptors alludes to stoichiometric-dependent action of the α-conotoxin, Vc1.1", Biochemical Pharmacology, 2014, p. 131-140, vol. 89.

(Continued)

Primary Examiner — Yong D Pak

(57) ABSTRACT

Expression systems for the expression of an α9α10 nicotinic acetylcholine receptor (nAChR) are described. Also described are methods of using the expression systems to identify agonists, antagonists, or allosteric modulators of an α9α10 nAChR.

6 Claims, 4 Drawing Sheets

Specification includes a Sequence Listing.

(56) References Cited

OTHER PUBLICATIONS

International Search Report and Written Opinion for International Application No. PCT/EP2020/063687 dated Aug. 5, 2020.
Ausubel et al., "Current Protocols In Molecular Biology", a joint venture between Greene Publishing Associates, Inc. and John Wiley & Sons Inc., 4955 p. 2003.
Bagdas et al., "The role of alpha5 nicotinic acetylcholine receptors in mouse models of chronic inflammatory and neuropathic pain", Biochemical Pharmacology, vol. 97, pp. 590-600, Apr. 28, 2015.
Ben-David et al., "RIC-3 expression and splicing regulate nAChR functional expression", Molecular Brain, vol. 9, 9 pages, Apr. 29, 2016.
Brunello Lorne et al: "Different efficiency of auxiliary/chaperone proteins to promote the functional reconstitution of honeybee glutamate and acetylcholine receptors in Xenopus laevis oocytes", Insect Molecular Biology, vol. 31, No. 5, pp. 620-633, XP93037104 GB ISSN: 0962-1075,Oct. 1, 2022 (Oct. 1, 2022).
Crespi et al., "Proteins and chemical chaperones involved in neuronal nicotinic receptor expression and function: an update", Brit Journal of Pharmacology, vol. 175, pp. 1869-1879, 2017.
Daly et al., "Alkaloids from Frog Skin: the Discovery of Epibatidine and the Potential for Developing Novel Non-Opioid Analgesics", Nat. Prod. Rep., vol. 17, pp. 131-135, 2000.
Daniel K. et al., "Functional a6 4 acetylcholine receptor expression enables pharmacological testing of nicotinic agonists with analgesic properties", The Journal of Clinical Investigation, vol. 130, No. 11, pp. 6158-6170, Nov. 2020.
Fowler et al., "Habenular a5 nicotinic receptors subunit signalling controls nicotine intake", Nature, vol. 471, pp. 597-601, Mar. 31, 2011.
Gotti et al., "Neuronal nicotinic receptors: from structure to pathology", Progress in Neurobiology, vol. 74, pp. 363-396, 2004.
Grant et al., "Proteins for increased surface expression of the a6 4 nicotinic acetylcholine receptor: nothing but good news?", The Journal of Clinical Investigation, vol. 130, No. 11, pp. 5685-5687, Nov. 2020.
Gu S. et al., "Brain a7 Nicotinic Acetylcholine Receptor Assembly Requires NACHO", Neuron, vol. 89, pp. 948-955, Mar. 2, 2016.
Gu S. et al., "a6-Containing Nicotinic Acetylcholine Receptor Reconstitution Involves Mechanistically Distinct Accessory Components", Cell Reports, vol. 26, pp. 866-874, Jan. 22, 2019.
Gu Shenyan et al."Hair cell [alpha] 9 [alpha] 10 nicotinic acetylcholinereceptor functional expression regulated by ligand binding and deafness gene products", Proceedings of the National Academy Ofsciences,Url: https://www.ncbi.nlm.nih.gov/pmc/articles/PMC7533656/pdf/pnas.202013762.pdf, vol. 117, No. 39 XP93037102, ISSN: 0027-8424 ,24534-24544 pages, Sep. 29, 2020 (Sep. 29, 2020).
Hone et al., "Nicotinic acetylcholine receptors in dorsal root ganglion neurons include the a6 4* subtype", The FASEB Journal, vol. 26, pp. 917-926, Feb. 2012.
Hone et al., "Nicotinic Acetylcholine Receptors in Neuropathic and Inflammatory Pain", FEBS Letters, vol. 592, pp. 1045-1062, 2018.
International search report and written opinion for PCT/EP2023/053378 , dated May 2, 2023, 17 pgs.
International Search Report and Written Opinion for PCT/EP2022/060744, dated Aug. 2, 2022,22 pages.
International Search Report and Written Opinion for PCT/EP2022/060765, dated Aug. 26, 2022, 17 Pages.
Kweon et al., "NACHO Engages N-Glycosylation ER Chaperone Pathways for a7 Nicotinic Receptor Assembly", Cell Reports, vol. 32, 17 pages, Aug. 11, 2020.
Maskos, "The nicotinic receptor alpha5 coding polymorphism rs16969968 as a major target in disease: Functional dissection and remaining challenges", Journal of Neurochemistry, vol. 154, pp. 241-250, 2020.
Matta et al., "Nicotinic acetylcholine receptor redux: Discovery of accessories opens therapeutic vistas", Science, vol. 373, 10 pages, Aug. 13, 2021.
Millar Ns, "RIC-3: a nicotinic acetylcholine receptor chaperone", The British Journal of Pharmacology, vol. 153, pp. S177-S183, 2008.
Rowbotham et al., "A randomized, double-blind, place bo-controlled trial evaluating the efficacy and safety of ABT-594 in patients with diabetic peripheral neuropathic pain", vol. 146 Issue 03, pp. 245-252, Dec. 2009.
Salas et al., "Nicotinic Receptors in the Habenulo-Interpeduncular System Are Necessary for Nicotine Withdrawal in Mice", The Journal of Neuroscience, vol. 29 Issue 10, pp. 3014-3018, Mar. 2009.
Scholze et al., "The a5 Nicotinic Acetylcholine Receptor Subunit Differentially Modulates a4 2* and a3 4* Receptors", Frontiers in Synaptic Neuroscience, vol. 12, Article 607959, 24 pages, Dec. 2020.
Srinivasan R et al., "Pharmacological chaperoning of nAChRs: A therapeutic target for Parkinson's disease", Pharmacol Res., vol. 83, 20 pages, May 2014.
Wieskopf et al., "The nicotinic a6 subunit gene determines variability in chronic pain sensitivity via cross-inhibition of P2X2/3 receptors", Science Translational Medicine, vol. 7 Issue 287, 287ra72, 16 pages, May 13, 2015.
Yang et al., "Mysterious a6-containing nAChRs: function, pharmacology, and pathophysiology", Acta Pharmacol Sin, vol. 30 Issue 6, pp. 740-751, Jun. 2009.

* cited by examiner

α9α10+TMIE

α9α10+CHAT+TMIE

α9α10+CHAT

α9α10+TMIE

α9α10+CHAT+TMIE

SEQUENCE LISTING

<160> NUMBER OF SEQ ID NOS: 10

<210> SEQ ID NO 1
<211> LENGTH: 479
<212> TYPE: PRT
<213> ORGANISM: Homo sapiens

<400> SEQUENCE: 1

Met Asn Trp Ser His Ser Cys Ile Ser Phe Cys Trp Ile Tyr Phe Ala
1               5                   10                  15

Ala Ser Arg Leu Arg Ala Ala Glu Thr Ala Asp Gly Lys Tyr Ala Gln
            20                  25                  30

Lys Leu Phe Asn Asp Leu Phe Glu Asp Tyr Ser Asn Ala Leu Arg Pro
        35                  40                  45

Val Glu Asp Thr Asp Lys Val Leu Asn Val Thr Leu Gln Ile Thr Leu
    50                  55                  60

Ser Gln Ile Lys Asp Met Asp Glu Arg Asn Gln Ile Leu Thr Ala Tyr
65                  70                  75                  80

Leu Trp Ile Arg Gln Ile Trp His Asp Ala Tyr Leu Thr Trp Asp Arg
                85                  90                  95

Asp Gln Tyr Asp Gly Leu Asp Ser Ile Arg Ile Pro Ser Asp Leu Val
            100                 105                 110

Trp Arg Pro Asp Ile Val Leu Tyr Asn Lys Ala Asp Asp Glu Ser Ser
        115                 120                 125

Glu Pro Val Asn Thr Asn Val Val Leu Arg Tyr Asp Gly Leu Ile Thr
    130                 135                 140

Trp Asp Ala Pro Ala Ile Thr Lys Ser Ser Cys Val Val Asp Val Thr
145                 150                 155                 160

Tyr Phe Pro Phe Asp Asn Gln Gln Cys Asn Leu Thr Phe Gly Ser Trp
                165                 170                 175

Thr Tyr Asn Gly Asn Gln Val Asp Ile Phe Asn Ala Leu Asp Ser Gly
            180                 185                 190

Asp Leu Ser Asp Phe Ile Glu Asp Val Glu Trp Glu Val His Gly Met
        195                 200                 205

Pro Ala Val Lys Asn Val Ile Ser Tyr Gly Cys Cys Ser Glu Pro Tyr
    210                 215                 220

Pro Asp Val Thr Phe Thr Leu Leu Leu Lys Arg Arg Ser Ser Phe Tyr
225                 230                 235                 240

Ile Val Asn Leu Leu Ile Pro Cys Val Leu Ile Ser Phe Leu Ala Pro
                245                 250                 255

Leu Ser Phe Tyr Leu Pro Ala Ala Ser Gly Glu Lys Val Ser Leu Gly
            260                 265                 270

Val Thr Ile Leu Leu Ala Met Thr Val Phe Gln Leu Met Val Ala Glu
        275                 280                 285

Ile Met Pro Ala Ser Glu Asn Val Pro Leu Ile Gly Lys Tyr Tyr Ile
    290                 295                 300

Ala Thr Met Ala Leu Ile Thr Ala Ser Thr Ala Leu Thr Ile Met Val
305                 310                 315                 320

Met Asn Ile His Phe Cys Gly Ala Glu Ala Arg Pro Val Pro His Trp
                325                 330                 335

Ala Arg Val Val Ile Leu Lys Tyr Met Ser Arg Val Leu Phe Val Tyr
            340                 345                 350

Asp Val Gly Glu Ser Cys Leu Ser Pro His His Ser Arg Glu Arg Asp
        355                 360                 365

```
His Leu Thr Lys Val Tyr Ser Lys Leu Pro Glu Ser Asn Leu Lys Ala
    370                 375                 380

Ala Arg Asn Lys Asp Leu Ser Arg Lys Asp Met Asn Lys Arg Leu
385                 390                 395                 400

Lys Asn Asp Leu Gly Cys Gln Gly Lys Asn Pro Gln Glu Ala Glu Ser
                405                 410                 415

Tyr Cys Ala Gln Tyr Lys Val Leu Thr Arg Asn Ile Glu Tyr Ile Ala
                420                 425                 430

Lys Cys Leu Lys Asp His Lys Ala Thr Asn Ser Lys Gly Ser Glu Trp
            435                 440                 445

Lys Lys Val Ala Lys Val Ile Asp Arg Phe Met Trp Ile Phe Phe
450                 455                 460

Ile Met Val Phe Val Met Thr Ile Leu Ile Ile Ala Arg Ala Asp
465                 470                 475

<210> SEQ ID NO 2
<211> LENGTH: 450
<212> TYPE: PRT
<213> ORGANISM: Homo sapiens

<400> SEQUENCE: 2

Met Gly Leu Arg Ser His His Leu Ser Leu Gly Leu Leu Leu Phe
1               5                   10                  15

Leu Leu Pro Ala Glu Cys Leu Gly Ala Glu Gly Arg Leu Ala Leu Lys
                20                  25                  30

Leu Phe Arg Asp Leu Phe Ala Asn Tyr Thr Ser Ala Leu Arg Pro Val
                35                  40                  45

Ala Asp Thr Asp Gln Thr Leu Asn Val Thr Leu Glu Val Thr Leu Ser
50                  55                  60

Gln Ile Ile Asp Met Asp Glu Arg Asn Gln Val Leu Thr Leu Tyr Leu
65                  70                  75                  80

Trp Ile Arg Gln Glu Trp Thr Asp Ala Tyr Leu Arg Trp Asp Pro Asn
                85                  90                  95

Ala Tyr Gly Gly Leu Asp Ala Ile Arg Ile Pro Ser Ser Leu Val Trp
                100                 105                 110

Arg Pro Asp Ile Val Leu Tyr Asn Lys Ala Asp Ala Gln Pro Pro Gly
                115                 120                 125

Ser Ala Ser Thr Asn Val Val Leu Arg His Asp Gly Ala Val Arg Trp
130                 135                 140

Asp Ala Pro Ala Ile Thr Arg Ser Ser Cys Arg Val Asp Val Ala Ala
145                 150                 155                 160

Phe Pro Phe Asp Ala Gln His Cys Gly Leu Thr Phe Gly Ser Trp Thr
                165                 170                 175

His Gly Gly His Gln Leu Asp Val Arg Pro Arg Gly Ala Ala Ala Ser
                180                 185                 190

Leu Ala Asp Phe Val Glu Asn Val Glu Trp Arg Val Leu Gly Met Pro
                195                 200                 205

Ala Arg Arg Arg Val Leu Thr Tyr Gly Cys Cys Ser Glu Pro Tyr Pro
210                 215                 220

Asp Val Thr Phe Thr Leu Leu Leu Arg Arg Arg Ala Ala Ala Tyr Val
225                 230                 235                 240

Cys Asn Leu Leu Leu Pro Cys Val Leu Ile Ser Leu Leu Ala Pro Leu
                245                 250                 255

Ala Phe His Leu Pro Ala Asp Ser Gly Glu Lys Val Ser Leu Gly Val
                260                 265                 270
```

```
Thr Val Leu Leu Ala Leu Thr Val Phe Gln Leu Leu Ala Glu Ser
        275                 280                 285
Met Pro Pro Ala Glu Ser Val Pro Leu Ile Gly Lys Tyr Tyr Met Ala
290                 295                 300
Thr Met Thr Met Val Thr Phe Ser Thr Ala Leu Thr Ile Leu Ile Met
305                 310                 315                 320
Asn Leu His Tyr Cys Gly Pro Ser Val Arg Pro Val Pro Ala Trp Ala
                    325                 330                 335
Arg Ala Leu Leu Leu Gly His Leu Ala Arg Gly Leu Cys Val Arg Glu
                340                 345                 350
Arg Gly Glu Pro Cys Gly Gln Ser Arg Pro Pro Glu Leu Ser Pro Ser
            355                 360                 365
Pro Gln Ser Pro Glu Gly Gly Ala Gly Pro Ala Gly Pro Cys His
        370                 375                 380
Glu Pro Arg Cys Leu Cys Arg Gln Glu Ala Leu Leu His His Val Ala
385                 390                 395                 400
Thr Ile Ala Asn Thr Phe Arg Ser His Arg Ala Ala Gln Arg Cys His
                    405                 410                 415
Glu Asp Trp Lys Arg Leu Ala Arg Val Met Asp Arg Phe Phe Leu Ala
                420                 425                 430
Ile Phe Phe Ser Met Ala Leu Val Met Ser Leu Leu Val Leu Val Gln
                435                 440                 445
Ala Leu
    450

<210> SEQ ID NO 3
<211> LENGTH: 630
<212> TYPE: PRT
<213> ORGANISM: Homo sapiens

<400> SEQUENCE: 3

Met Ala Ala Lys Thr Pro Ser Ser Glu Glu Ser Gly Leu Pro Lys Leu
1               5                   10                  15
Pro Val Pro Pro Leu Gln Gln Thr Leu Ala Thr Tyr Leu Gln Cys Met
                20                  25                  30
Arg His Leu Val Ser Glu Glu Gln Phe Arg Lys Ser Gln Ala Ile Val
            35                  40                  45
Gln Gln Phe Gly Ala Pro Gly Gly Leu Gly Glu Thr Leu Gln Gln Lys
        50                  55                  60
Leu Leu Glu Arg Gln Glu Lys Thr Ala Asn Trp Val Ser Glu Tyr Trp
65                  70                  75                  80
Leu Asn Asp Met Tyr Leu Asn Asn Arg Leu Ala Leu Pro Val Asn Ser
                85                  90                  95
Ser Pro Ala Val Ile Phe Ala Arg Gln His Phe Pro Gly Thr Asp Asp
                100                 105                 110
Gln Leu Arg Phe Ala Ala Ser Leu Ile Ser Gly Val Leu Ser Tyr Lys
            115                 120                 125
Ala Leu Leu Asp Ser His Ser Ile Pro Thr Asp Cys Ala Lys Gly Gln
        130                 135                 140
Leu Ser Gly Gln Pro Leu Cys Met Lys Gln Tyr Tyr Gly Leu Phe Ser
145                 150                 155                 160
Ser Tyr Arg Leu Pro Gly His Thr Gln Asp Thr Leu Val Ala Gln Asn
                165                 170                 175
Ser Ser Ile Met Pro Glu Pro Glu His Val Ile Val Ala Cys Cys Asn
```

```
                180               185               190
    Gln Phe Phe Val Leu Asp Val Val Ile Asn Phe Arg Arg Leu Ser Glu
                    195               200               205
    Gly Asp Leu Phe Thr Gln Leu Arg Lys Ile Val Lys Met Ala Ser Asn
            210               215               220
    Glu Asp Glu Arg Leu Pro Pro Ile Gly Leu Leu Thr Ser Asp Gly Arg
    225               230               235               240
    Ser Glu Trp Ala Glu Ala Arg Thr Val Leu Val Lys Asp Ser Thr Asn
                    245               250               255
    Arg Asp Ser Leu Asp Met Ile Glu Arg Cys Ile Cys Leu Val Cys Leu
                260               265               270
    Asp Ala Pro Gly Gly Val Glu Leu Ser Asp Thr His Arg Ala Leu Gln
                275               280               285
    Leu Leu His Gly Gly Gly Tyr Ser Lys Asn Gly Ala Asn Arg Trp Tyr
                290               295               300
    Asp Lys Ser Leu Gln Phe Val Val Gly Arg Asp Gly Thr Cys Gly Val
    305               310               315               320
    Val Cys Glu His Ser Pro Phe Asp Gly Ile Val Leu Val Gln Cys Thr
                    325               330               335
    Glu His Leu Leu Lys His Met Thr Gln Ser Ser Arg Lys Leu Ile Arg
                340               345               350
    Ala Asp Ser Val Ser Glu Leu Pro Ala Pro Arg Arg Leu Arg Trp Lys
                355               360               365
    Cys Ser Pro Glu Ile Gln Gly His Leu Ala Ser Ser Ala Glu Lys Leu
                370               375               380
    Gln Arg Ile Val Lys Asn Leu Asp Phe Ile Val Tyr Lys Phe Asp Asn
    385               390               395               400
    Tyr Gly Lys Thr Phe Ile Lys Lys Gln Lys Cys Ser Pro Asp Ala Phe
                    405               410               415
    Ile Gln Val Ala Leu Gln Leu Ala Phe Tyr Arg Leu His Arg Arg Leu
                420               425               430
    Val Pro Thr Tyr Glu Ser Ala Ser Ile Arg Arg Phe Gln Glu Gly Arg
                435               440               445
    Val Asp Asn Ile Arg Ser Ala Thr Pro Glu Ala Leu Ala Phe Val Arg
                450               455               460
    Ala Val Thr Asp His Lys Ala Val Pro Ala Ser Glu Lys Leu Leu
    465               470               475               480
    Leu Leu Lys Asp Ala Ile Arg Ala Gln Thr Ala Tyr Thr Val Met Ala
                    485               490               495
    Ile Thr Gly Met Ala Ile Asp Asn His Leu Leu Ala Leu Arg Glu Leu
                500               505               510
    Ala Arg Ala Met Cys Lys Glu Leu Pro Glu Met Phe Met Asp Glu Thr
                515               520               525
    Tyr Leu Met Ser Asn Arg Phe Val Leu Ser Thr Ser Gln Val Pro Thr
                530               535               540
    Thr Thr Glu Met Phe Cys Cys Tyr Gly Pro Val Val Pro Asn Gly Tyr
    545               550               555               560
    Gly Ala Cys Tyr Asn Pro Gln Pro Glu Thr Ile Leu Phe Cys Ile Ser
                    565               570               575
    Ser Phe His Ser Cys Lys Glu Thr Ser Ser Lys Phe Ala Lys Ala
                580               585               590
    Val Glu Glu Ser Leu Ile Asp Met Arg Asp Leu Cys Ser Leu Leu Pro
                595               600               605
```

Pro Thr Glu Ser Lys Pro Leu Ala Thr Lys Glu Lys Ala Thr Arg Pro
    610                 615                 620

Ser Gln Gly His Gln Pro
625                 630

<210> SEQ ID NO 4
<211> LENGTH: 156
<212> TYPE: PRT
<213> ORGANISM: Homo sapiens

<400> SEQUENCE: 4

Met Ala Gly Trp Pro Gly Ala Gly Pro Leu Cys Val Leu Gly Gly Ala
1               5                   10                  15

Ala Leu Gly Val Cys Leu Ala Gly Val Ala Gly Gln Leu Val Glu Pro
            20                  25                  30

Ser Thr Ala Pro Pro Lys Pro Lys Pro Pro Leu Thr Lys Glu Thr
        35                  40                  45

Val Val Phe Trp Asp Met Arg Leu Trp His Val Gly Ile Phe Ser
    50                  55                  60

Leu Phe Val Leu Ser Ile Ile Ile Thr Leu Cys Cys Val Phe Asn Cys
65                  70                  75                  80

Arg Val Pro Arg Thr Arg Lys Glu Ile Glu Ala Arg Tyr Leu Gln Arg
                85                  90                  95

Lys Ala Ala Lys Met Tyr Thr Asp Lys Leu Glu Thr Val Pro Pro Leu
            100                 105                 110

Asn Glu Leu Thr Glu Val Pro Gly Glu Asp Lys Lys Lys Lys Lys
        115                 120                 125

Lys Lys Lys Asp Ser Val Asp Thr Val Ala Ile Lys Val Glu Glu Asp
    130                 135                 140

Glu Lys Asn Glu Ala Lys Lys Lys Gly Glu Lys
145                 150                 155

<210> SEQ ID NO 5
<211> LENGTH: 1023
<212> TYPE: PRT
<213> ORGANISM: Homo sapiens

<400> SEQUENCE: 5

Met Cys Ala Arg Met Ala Gly Arg Thr Thr Ala Ala Pro Arg Gly Pro
1               5                   10                  15

Tyr Gly Pro Trp Leu Cys Leu Leu Val Ala Leu Ala Leu Asp Val Val
            20                  25                  30

Arg Val Asp Cys Gly Gln Ala Pro Leu Asp Pro Val Tyr Leu Pro Ala
        35                  40                  45

Ala Leu Glu Leu Leu Asp Ala Pro Glu His Phe Arg Val Gln Gln Val
    50                  55                  60

Gly His Tyr Pro Pro Ala Asn Ser Ser Leu Ser Ser Arg Ser Glu Thr
65                  70                  75                  80

Phe Leu Leu Leu Gln Pro Trp Pro Arg Ala Gln Pro Leu Leu Arg Ala
                85                  90                  95

Ser Tyr Pro Pro Phe Ala Thr Gln Gln Val Val Pro Arg Val Thr
            100                 105                 110

Glu Pro His Gln Arg Pro Val Pro Trp Asp Val Arg Ala Val Ser Val
        115                 120                 125

Glu Ala Ala Val Thr Pro Ala Glu Pro Tyr Ala Arg Val Leu Phe His
    130                 135                 140

```
Leu Lys Gly Gln Asp Trp Pro Pro Gly Ser Gly Ser Leu Pro Cys Ala
145                 150                 155                 160

Arg Leu His Ala Thr His Pro Ala Gly Thr Ala His Gln Ala Cys Arg
            165                 170                 175

Phe Gln Pro Ser Leu Gly Ala Cys Val Val Glu Leu Glu Leu Pro Ser
            180                 185                 190

His Trp Phe Ser Gln Ala Ser Thr Thr Arg Ala Glu Leu Ala Tyr Thr
            195                 200                 205

Leu Glu Pro Ala Ala Glu Gly Pro Gly Gly Cys Gly Ser Gly Glu Glu
            210                 215                 220

Asn Asp Pro Gly Glu Gln Ala Leu Pro Val Gly Gly Val Glu Leu Arg
225                 230                 235                 240

Pro Ala Asp Pro Pro Gln Tyr Gln Glu Val Pro Leu Asp Glu Ala Val
            245                 250                 255

Thr Leu Arg Val Pro Asp Met Pro Val Arg Pro Gly Gln Leu Phe Ser
            260                 265                 270

Ala Thr Leu Leu Leu Arg His Asn Phe Thr Ala Ser Leu Leu Thr Leu
            275                 280                 285

Arg Ile Lys Val Lys Lys Gly Leu His Val Thr Ala Ala Arg Pro Ala
290                 295                 300

Gln Pro Thr Leu Trp Thr Ala Lys Leu Asp Arg Phe Lys Gly Ser Arg
305                 310                 315                 320

His His Thr Thr Leu Ile Thr Cys His Arg Ala Gly Leu Thr Glu Pro
            325                 330                 335

Asp Ser Ser Pro Leu Glu Leu Ser Glu Phe Leu Trp Val Asp Phe Val
            340                 345                 350

Val Glu Asn Ser Thr Gly Gly Val Ala Val Thr Arg Pro Val Thr
            355                 360                 365

Trp Gln Leu Glu Tyr Pro Gly Gln Ala Pro Glu Ala Glu Lys Asp Lys
            370                 375                 380

Met Val Trp Glu Ile Leu Val Ser Glu Arg Asp Ile Arg Ala Leu Ile
385                 390                 395                 400

Pro Leu Ala Lys Ala Glu Glu Leu Val Asn Thr Ala Pro Leu Thr Gly
                405                 410                 415

Val Pro Gln His Val Pro Val Arg Leu Val Thr Val Asp Gly Gly Gly
            420                 425                 430

Ala Leu Val Glu Val Thr Glu His Val Gly Cys Glu Ser Ala Asn Thr
            435                 440                 445

Gln Val Leu Gln Val Ser Glu Ala Cys Asp Ala Val Phe Val Ala Gly
            450                 455                 460

Lys Glu Ser Arg Gly Ala Arg Gly Val Arg Val Asp Phe Trp Trp Arg
465                 470                 475                 480

Arg Leu Arg Ala Ser Leu Arg Leu Thr Val Trp Ala Pro Leu Leu Pro
            485                 490                 495

Leu Arg Ile Glu Leu Thr Asp Thr Thr Leu Glu Gln Val Arg Gly Trp
            500                 505                 510

Arg Val Pro Gly Pro Ala Glu Gly Pro Ala Glu Pro Ala Ala Glu Ala
            515                 520                 525

Ser Asp Glu Ala Glu Arg Arg Ala Arg Gly Cys His Leu Gln Tyr Gln
            530                 535                 540

Arg Ala Gly Val Arg Phe Leu Ala Pro Phe Ala Ala His Pro Leu Asp
545                 550                 555                 560
```

```
Gly Gly Arg Arg Leu Thr His Leu Leu Gly Pro Asp Trp Leu Leu Asp
            565                 570                 575
Val Ser His Leu Val Ala Pro His Ala Arg Val Leu Asp Ser Arg Val
        580                 585                 590
Ala Ser Leu Glu Gly Gly Arg Val Val Gly Arg Glu Pro Gly Val
    595                 600                 605
Thr Ser Ile Glu Val Arg Ser Pro Leu Ser Asp Ser Ile Leu Gly Glu
        610                 615                 620
Gln Ala Leu Ala Val Thr Asp Asp Lys Val Ser Val Leu Glu Leu Arg
625                 630                 635                 640
Val Gln Pro Val Met Gly Ile Ser Leu Thr Leu Ser Arg Gly Thr Ala
                645                 650                 655
His Pro Gly Glu Val Thr Ala Thr Cys Trp Ala Gln Ser Ala Leu Pro
                660                 665                 670
Ala Pro Lys Gln Glu Val Ala Leu Ser Leu Trp Leu Ser Phe Ser Asp
            675                 680                 685
His Thr Val Ala Pro Ala Glu Leu Tyr Asp Arg Arg Asp Leu Gly Leu
        690                 695                 700
Ser Val Ser Ala Glu Glu Pro Gly Ala Ile Leu Pro Ala Glu Gln
705                 710                 715                 720
Gly Ala Gln Leu Gly Val Val Ser Gly Ala Gly Ala Glu Gly Leu
                725                 730                 735
Pro Leu His Val Ala Leu His Pro Glu Pro Cys Arg Arg Gly Arg
                740                 745                 750
His Arg Val Pro Leu Ala Ser Gly Thr Ala Trp Leu Gly Leu Pro Pro
            755                 760                 765
Ala Ser Thr Pro Ala Pro Ala Leu Pro Ser Ser Pro Ala Trp Ser Pro
        770                 775                 780
Pro Ala Thr Glu Ala Thr Met Gly Gly Lys Arg Gln Val Ala Gly Ser
785                 790                 795                 800
Val Gly Gly Asn Thr Gly Val Arg Gly Lys Phe Glu Arg Ala Glu Glu
                805                 810                 815
Glu Ala Arg Lys Glu Glu Thr Glu Ala Arg Glu Glu Glu Glu Glu
            820                 825                 830
Glu Glu Glu Met Val Pro Ala Pro Gln His Val Thr Glu Leu Glu Leu
        835                 840                 845
Gly Met Tyr Ala Leu Leu Gly Val Phe Cys Val Ala Ile Phe Ile Phe
    850                 855                 860
Leu Val Asn Gly Val Val Phe Val Leu Arg Tyr Gln Arg Lys Glu Pro
865                 870                 875                 880
Pro Asp Ser Ala Thr Asp Pro Thr Ser Pro Gln Pro His Asn Trp Val
                885                 890                 895
Trp Leu Gly Thr Asp Gln Glu Glu Leu Ser Arg Gln Leu Asp Arg Gln
                900                 905                 910
Ser Pro Gly Pro Pro Lys Gly Glu Gly Ser Cys Pro Cys Glu Ser Gly
        915                 920                 925
Gly Gly Gly Glu Ala Pro Thr Leu Ala Pro Gly Pro Pro Gly Gly Thr
    930                 935                 940
Thr Ser Ser Ser Ser Thr Leu Ala Arg Lys Ala Gly Gly Arg Arg
945                 950                 955                 960
Lys Arg Val Glu Phe Val Thr Phe Ala Pro Ala Pro Ala Gln Ser
                965                 970                 975
Pro Glu Glu Pro Val Gly Ala Pro Ala Val Gln Ser Ile Leu Val Ala
```

```
                    980             985              990
Gly Glu Glu Asp Ile Arg Trp Val Cys Glu Asp Met Gly Leu Lys Asp
            995              1000            1005

Pro Glu Glu Leu Arg Asn Tyr Met Glu Arg Ile Arg Gly Ser Ser
        1010            1015            1020

<210> SEQ ID NO 6
<211> LENGTH: 1108
<212> TYPE: PRT
<213> ORGANISM: Homo sapiens

<400> SEQUENCE: 6

Met Arg Ser Glu Gly Ala Ala Pro Gly Pro Ala Ala Pro Leu Cys Gly
1               5                   10                  15

Ala Leu Ser Leu Leu Leu Gly Ala Leu Leu Gly Lys Val Ile Glu Gly
            20                  25                  30

His Gly Val Thr Asp Asn Ile Gln Arg Phe Ser Ser Leu Pro Pro Tyr
        35                  40                  45

Leu Pro Val Ser Tyr His Ile Leu Arg Ala Glu Thr Ser Phe Phe Leu
    50                  55                  60

Lys Glu Ala Asn Gln Asp Leu Leu Arg Asn Ser Ser Leu Gln Ala Arg
65                  70                  75                  80

Val Glu Ser Phe Phe Thr Tyr Lys Thr Arg Gln Pro Pro Val Leu Asn
                85                  90                  95

Ala Ser Tyr Gly Pro Phe Ser Val Glu Lys Val Val Pro Leu Asp Leu
            100                 105                 110

Met Leu Thr Ser Asn Phe Leu Gly Pro Thr Asn Lys Phe Ser Phe Asp
        115                 120                 125

Trp Lys Leu Lys Ala His Ile Leu Arg Asp Lys Val Tyr Leu Ser Arg
    130                 135                 140

Pro Lys Val Gln Val Leu Phe His Ile Met Gly Arg Asp Trp Asp Asp
145                 150                 155                 160

His Gly Ala Gly Glu Lys Leu Pro Cys Leu Arg Val Phe Ala Phe Arg
                165                 170                 175

Glu Thr Arg Glu Val Arg Gly Ser Cys Arg Leu Lys Gly Asp Leu Gly
            180                 185                 190

Leu Cys Val Ala Glu Leu Glu Leu Leu Ser Ser Trp Phe Ser Ala Pro
        195                 200                 205

Thr Val Gly Ala Gly Arg Lys Lys Ser Met Asp Gln Pro Glu Gly Thr
    210                 215                 220

Pro Val Glu Leu Tyr Tyr Thr Val His Pro Gly Asn Glu Arg Gly Asp
225                 230                 235                 240

Cys Ala Gly Gly Asp Phe Arg Lys Gly Asn Ala Ile Arg Pro Gly Lys
                245                 250                 255

Asp Gly Leu Glu Glu Thr Thr Ser His Leu Gln Arg Ile Gly Thr Val
            260                 265                 270

Gly Leu Tyr Arg Ala Gln Asp Ser Ala Gln Leu Ser Glu Leu Arg Leu
        275                 280                 285

Asp Gly Asn Val Val Ile Trp Leu Pro Ser Arg Pro Val Lys Gln Gly
    290                 295                 300

Glu Val Val Thr Ala Tyr Val Thr Ile Ser Ser Asn Ser Ser Val Asp
305                 310                 315                 320

Leu Phe Ile Leu Arg Ala Lys Val Lys Lys Gly Val Asn Ile Leu Ser
                325                 330                 335
```

Ala Gln Thr Arg Glu Pro Arg Gln Trp Gly Val Lys Gln Glu Val Gly
                340                 345                 350

Ser Gly Gly Lys His Val Thr Ala Thr Val Ala Cys Gln Arg Leu Gly
            355                 360                 365

Pro Ser Pro Arg Asn Arg Ser Ser Ser Leu Phe Asn Glu Val Val Gln
        370                 375                 380

Met Asn Phe Glu Ile Ala Ser Phe Ser Ser Leu Ser Gly Thr Gln Pro
385                 390                 395                 400

Ile Thr Trp Gln Val Glu Tyr Pro Arg Lys Gly Thr Thr Asp Ile Ala
                405                 410                 415

Val Ser Glu Ile Phe Val Ser Gln Lys Asp Leu Val Gly Ile Val Pro
            420                 425                 430

Leu Ala Met Asp Thr Glu Ile Leu Asn Thr Ala Val Leu Thr Gly Lys
        435                 440                 445

Thr Val Ala Met Pro Ile Lys Val Ser Val Glu Glu Asn Ser Ala
    450                 455                 460

Val Met Asp Ile Ser Glu Ser Val Glu Cys Lys Ser Thr Asp Glu Asp
465                 470                 475                 480

Val Ile Lys Val Ser Glu Arg Cys Asp Tyr Ile Phe Val Asn Gly Lys
                485                 490                 495

Glu Ile Lys Gly Lys Met Asp Ala Val Val Asn Phe Thr Tyr Gln Tyr
            500                 505                 510

Leu Ser Ala Pro Leu Cys Val Thr Val Trp Val Pro Arg Leu Pro Leu
        515                 520                 525

Gln Ile Glu Val Ser Asp Thr Glu Leu Ser Gln Ile Lys Gly Trp Arg
    530                 535                 540

Val Pro Ile Val Thr Asn Lys Arg Pro Thr Arg Glu Ser Glu Asp Glu
545                 550                 555                 560

Asp Glu Glu Glu Arg Arg Gly Arg Gly Cys Ala Leu Gln Tyr Gln His
                565                 570                 575

Ala Thr Val Arg Val Leu Thr Gln Phe Val Ser Glu Gly Ala Gly Pro
            580                 585                 590

Trp Gly Gln Pro Asn Tyr Leu Leu Ser Pro Asn Trp Gln Phe Asp Ile
        595                 600                 605

Thr His Leu Val Ala Asp Phe Met Lys Leu Glu Glu Pro His Val Ala
    610                 615                 620

Thr Leu Gln Asp Ser Arg Val Leu Val Gly Arg Glu Val Gly Met Thr
625                 630                 635                 640

Thr Ile Gln Val Leu Ser Pro Leu Ser Asp Ser Ile Leu Ala Glu Lys
                645                 650                 655

Thr Ile Thr Val Leu Asp Asp Lys Val Ser Val Thr Asp Leu Ala Ile
            660                 665                 670

Gln Leu Val Ala Gly Leu Ser Val Ala Leu Tyr Pro Asn Ala Glu Asn
        675                 680                 685

Ser Lys Ala Val Thr Ala Val Thr Ala Glu Glu Val Leu Arg Thr
    690                 695                 700

Pro Lys Gln Glu Ala Val Phe Ser Thr Trp Leu Gln Phe Ser Asp Gly
705                 710                 715                 720

Ser Val Thr Pro Leu Asp Ile Tyr Asp Thr Lys Asp Phe Ser Leu Ala
                725                 730                 735

Ala Thr Ser Gln Asp Glu Ala Val Val Ser Val Pro Gln Pro Arg Ser
            740                 745                 750

Pro Arg Trp Pro Val Val Val Ala Glu Gly Glu Gly Gln Gly Pro Leu 755                 760                 765
Ile Arg Val Asp Met Thr Ile Ala Glu Ala Cys Gln Lys Ser Lys Arg
    770                 775                 780

Lys Ser Ile Leu Ala Val Gly Val Gly Asn Val Arg Val Lys Phe Gly
785                 790                 795                 800

Gln Asn Asp Ala Asp Ser Ser Pro Gly Gly Asp Tyr Glu Glu Asp Glu
                    805                 810                 815

Ile Lys Asn His Ala Ser Asp Arg Arg Gln Lys Gly Gln His His Glu
                820                 825                 830

Arg Thr Gly Gln Asp Gly His Leu Tyr Gly Ser Ser Pro Val Glu Arg
            835                 840                 845

Glu Glu Gly Ala Leu Arg Arg Ala Thr Thr Thr Ala Arg Ser Leu Leu
        850                 855                 860

Asp Asn Lys Val Val Lys Asn Ser Arg Ala Asp Gly Gly Arg Leu Ala
865                 870                 875                 880

Gly Glu Gly Gln Leu Gln Asn Ile Pro Ile Asp Phe Thr Asn Phe Pro
                    885                 890                 895

Ala His Val Asp Leu Pro Lys Ala Gly Ser Gly Leu Glu Glu Asn Asp
                900                 905                 910

Leu Val Gln Thr Pro Arg Gly Leu Ser Asp Leu Glu Ile Gly Met Tyr
            915                 920                 925

Ala Leu Leu Gly Val Phe Cys Leu Ala Ile Leu Val Phe Leu Ile Asn
        930                 935                 940

Cys Ala Thr Phe Ala Leu Lys Tyr Arg His Lys Gln Val Pro Leu Glu
945                 950                 955                 960

Gly Gln Ala Ser Met Thr His Ser His Asp Trp Val Trp Leu Gly Asn
                    965                 970                 975

Glu Ala Glu Leu Leu Glu Ser Met Gly Asp Ala Pro Pro Gln Asp
                980                 985                 990

Glu His Thr Thr Ile Ile Asp Arg Gly Pro Gly Ala Cys Glu Glu Ser
            995                 1000                1005

Asn His Leu Leu Leu Asn Gly Gly Ser His Lys His Val Gln Ser
       1010                1015                1020

Gln Ile His Arg Ser Ala Asp Ser Gly Gly Arg Gln Gly Arg Glu
       1025                1030                1035

Gln Lys Gln Asp Pro Leu His Ser Pro Thr Ser Lys Arg Lys Lys
       1040                1045                1050

Val Lys Phe Thr Thr Phe Thr Ile Pro Pro Asp Asp Ser Cys
       1055                1060                1065

Pro Thr Val Asn Ser Ile Val Ser Ser Asn Asp Glu Asp Ile Lys
       1070                1075                1080

Trp Val Cys Gln Asp Val Ala Val Gly Ala Pro Lys Glu Leu Arg
       1085                1090                1095

Asn Tyr Leu Glu Lys Leu Lys Asp Lys Ala
       1100                1105

<210> SEQ ID NO 7
<211> LENGTH: 1099
<212> TYPE: PRT
<213> ORGANISM: Homo sapiens

<400> SEQUENCE: 7

Met Cys Pro Ser Glu Met Gly Thr Leu Trp His His Trp Ser Pro Val
1               5                   10                  15

-continued

```
Leu Ile Ser Leu Ala Ala Leu Phe Ser Lys Val Thr Glu Gly Arg Gly
         20                  25                  30

Ile Leu Glu Ser Ile Gln Arg Phe Ser Leu Pro Thr Tyr Leu Pro
             35                  40                  45

Val Thr Tyr His Ile Asn Asn Ala Asp Val Ser Phe Phe Leu Lys Glu
         50                  55                  60

Ala Asn Gln Asp Ile Met Arg Asn Ser Ser Leu Gln Ser Arg Val Glu
65                  70                  75                  80

Ser Phe Leu Ile Tyr Lys Ser Arg Arg Leu Pro Val Leu Asn Ala Ser
                 85                  90                  95

Tyr Gly Pro Phe Ser Ile Glu Gln Val Val Pro Gln Asp Leu Met Leu
             100                 105                 110

Pro Ser Asn Pro Phe Gly Phe Thr Asn Lys Phe Ser Leu Asn Trp Lys
             115                 120                 125

Leu Lys Ala His Ile Leu Arg Asp Lys Val Tyr Leu Ser Arg Pro Lys
         130                 135                 140

Val Gln Val Leu Phe His Ile Met Gly Arg Asp Trp Asp Asp Arg Ser
145                 150                 155                 160

Ala Gly Glu Lys Leu Pro Cys Leu Arg Val Phe Ala Phe Arg Glu Thr
                 165                 170                 175

Arg Glu Val Arg Gly Ser Cys Arg Leu Gln Gly Asp Leu Gly Leu Cys
             180                 185                 190

Val Ala Glu Leu Glu Leu Leu Ser Ser Trp Phe Ser Pro Thr Val
         195                 200                 205

Val Ala Gly Arg Arg Lys Ser Val Asp Gln Pro Glu Gly Thr Pro Val
         210                 215                 220

Glu Leu Tyr Tyr Thr Val His Pro Gly Gly Glu Arg Gly Asp Cys Val
225                 230                 235                 240

Arg Glu Asp Ala Arg Arg Ser Asn Gly Ile Arg Thr Gly His Ser Asp
                 245                 250                 255

Ile Asp Glu Ser Gly Pro Pro Leu Gln Arg Ile Gly Ser Ile Phe Leu
             260                 265                 270

Tyr Gln Thr His Arg Lys Pro Ser Leu Arg Glu Leu Arg Leu Asp Asn
             275                 280                 285

Ser Val Ala Ile His Tyr Ile Pro Lys Thr Val Arg Lys Gly Asp Val
         290                 295                 300

Leu Thr Phe Pro Val Ser Ile Ser Arg Asn Ser Thr Glu Asp Arg Phe
305                 310                 315                 320

Thr Leu Arg Ala Lys Val Lys Lys Gly Val Asn Ile Ile Gly Val Arg
                 325                 330                 335

Ala Ser Ser Pro Ser Ile Trp Asp Val Lys Glu Arg Thr Asp Tyr Thr
             340                 345                 350

Gly Lys Tyr Ala Pro Ala Val Ile Val Cys Gln Lys Lys Ala Ala Gly
             355                 360                 365

Ser Glu Asn Ser Ala Asp Gly Ala Ser Tyr Glu Val Met Gln Ile Asp
         370                 375                 380

Val Glu Val Glu Glu Pro Gly Asp Leu Pro Ala Thr Gln Leu Val Thr
385                 390                 395                 400

Trp Gln Val Glu Tyr Pro Gly Glu Ile Thr Ser Asp Leu Gly Val Ser
                 405                 410                 415

Lys Ile Tyr Val Ser Pro Lys Asp Leu Ile Gly Val Val Pro Leu Ala
             420                 425                 430

Met Glu Ala Glu Ile Leu Asn Thr Ala Ile Leu Thr Gly Lys Thr Val
```

```
                435                 440                 445
Ala Val Pro Val Lys Val Val Ser Val Glu Asp Asp Gly Thr Val Thr
450                 455                 460
Glu Leu Leu Glu Ser Val Glu Cys Arg Ser Ser Asp Glu Asp Val Ile
465                 470                 475                 480
Lys Val Ser Asp Arg Cys Asp Tyr Val Phe Val Asn Gly Lys Glu Met
                485                 490                 495
Lys Gly Lys Val Asn Val Val Asn Phe Thr Tyr Gln His Leu Ser
                500                 505                 510
Ser Pro Leu Glu Met Thr Val Trp Val Pro Arg Leu Pro Leu Gln Ile
            515                 520                 525
Glu Val Ser Asp Thr Glu Leu Asn Gln Ile Lys Gly Trp Arg Val Pro
530                 535                 540
Ile Val Ser Ser Arg Arg Pro Ala Gly Asp Ser Glu Glu Glu Asp
545                 550                 555                 560
Asp Glu Arg Arg Gly Arg Gly Cys Thr Leu Gln Tyr Gln His Ala Met
                565                 570                 575
Val Arg Val Leu Thr Gln Phe Val Ala Glu Ala Ala Gly Pro Gly Gly
                580                 585                 590
His Leu Ala His Leu Leu Gly Ser Asp Trp Gln Val Asp Ile Thr Glu
            595                 600                 605
Leu Ile Asn Asp Phe Met Gln Val Glu Pro Arg Ile Ala Lys Leu
            610                 615                 620
Gln Gly Gly Gln Ile Leu Met Gly Gln Glu Leu Gly Met Thr Thr Ile
625                 630                 635                 640
Gln Ile Leu Ser Pro Leu Ser Asp Thr Ile Leu Ala Glu Lys Thr Ile
                645                 650                 655
Thr Val Leu Asp Glu Lys Val Thr Ile Thr Asp Leu Gly Val Gln Leu
                660                 665                 670
Val Thr Gly Leu Ser Leu Ser Leu Gln Leu Ser Pro Gly Ser Asn Arg
            675                 680                 685
Ala Ile Phe Ala Thr Ala Val Ala Gln Glu Leu Leu Gln Arg Pro Lys
            690                 695                 700
Gln Glu Ala Ala Ile Ser Cys Trp Val Gln Phe Ser Asp Gly Ser Val
705                 710                 715                 720
Thr Pro Leu Asp Ile Tyr Asp Gly Lys Asp Phe Ser Leu Met Ala Thr
                725                 730                 735
Ser Leu Asp Glu Lys Val Val Ser Ile His Gln Asp Pro Lys Phe Lys
            740                 745                 750
Trp Pro Ile Ile Ala Ala Glu Thr Glu Gly Gln Gly Thr Leu Val Lys
            755                 760                 765
Val Glu Met Val Ile Ser Glu Ser Cys Gln Lys Ser Lys Arg Lys Ser
            770                 775                 780
Val Leu Ala Val Gly Thr Ala Asn Ile Lys Val Lys Phe Gly Gln Asn
785                 790                 795                 800
Asp Ala Asn Pro Asn Thr Ser Asp Ser Arg His Thr Gly Ala Gly Val
                805                 810                 815
His Met Glu Asn Asn Val Ser Asp Arg Arg Pro Lys Lys Pro Ser Gln
            820                 825                 830
Glu Trp Gly Ser Gln Glu Gly Gln Tyr Tyr Gly Ser Ser Ser Met Gly
            835                 840                 845
Leu Met Glu Gly Arg Gly Thr Thr Asp Arg Ser Ile Leu Gln Lys
            850                 855                 860
```

-continued

```
Lys Lys Gly Gln Glu Ser Leu Leu Asp Asp Asn Ser His Leu Gln Thr
865                 870                 875                 880

Ile Pro Ser Asp Leu Thr Ser Phe Pro Ala Gln Val Asp Leu Pro Arg
                885                 890                 895

Ser Asn Gly Glu Met Asp Gly Asn Asp Leu Met Gln Ala Ser Lys Gly
            900                 905                 910

Leu Ser Asp Leu Glu Ile Gly Met Tyr Ala Leu Leu Gly Val Phe Cys
        915                 920                 925

Leu Ala Ile Leu Val Phe Leu Ile Asn Cys Val Thr Phe Ala Leu Lys
    930                 935                 940

Tyr Arg His Lys Gln Val Pro Phe Glu Glu Gln Glu Gly Met Ser His
945                 950                 955                 960

Ser His Asp Trp Val Gly Leu Ser Asn Arg Thr Glu Leu Leu Glu Asn
                965                 970                 975

His Ile Asn Phe Ala Ser Ser Gln Asp Glu Gln Ile Thr Ala Ile Asp
            980                 985                 990

Arg Gly Met Asp Phe Glu Glu Ser  Lys Tyr Leu Leu Ser  Thr Asn Ser
        995                1000                1005

Gln Lys  Ser Ile Asn Gly Gln  Leu Phe Lys Pro Leu  Gly Pro Ile
    1010                1015                1020

Ile Ile Asp Gly Lys Asp Gln  Lys Ser Glu Pro Pro   Thr Ser Pro
    1025                1030                1035

Thr Ser  Lys Arg Lys Arg Val  Lys Phe Thr Thr Phe  Thr Ala Val
    1040                1045                1050

Ser Ser  Asp Asp Glu Tyr Pro  Thr Arg Asn Ser Ile  Val Met Ser
    1055                1060                1065

Ser Glu  Asp Asp Ile Lys Trp  Val Cys Gln Asp Leu  Asp Pro Gly
    1070                1075                1080

Asp Cys  Lys Glu Leu His Asn  Tyr Met Glu Arg Leu  His Glu Asn
    1085                1090                1095

Val

<210> SEQ ID NO 8
<211> LENGTH: 1074
<212> TYPE: PRT
<213> ORGANISM: Homo sapiens

<400> SEQUENCE: 8

Met Ala Pro Gly Met Ser Gly Arg Gly Ala Ala Leu Leu Cys Leu
1               5                   10                  15

Ser Ala Leu Leu Ala His Ala Ser Gly Arg Ser His Pro Ala Ser Pro
                20                  25                  30

Ser Pro Pro Gly Pro Gln Ala Ser Pro Val Leu Pro Val Ser Tyr Arg
            35                  40                  45

Leu Ser His Thr Arg Leu Ala Phe Phe Leu Arg Glu Ala Arg Pro Pro
        50                  55                  60

Ser Pro Ala Val Ala Asn Ser Ser Leu Gln Arg Ser Glu Pro Phe Val
65                  70                  75                  80

Val Phe Gln Thr Lys Glu Leu Pro Val Leu Asn Val Ser Leu Gly Pro
                85                  90                  95

Phe Ser Thr Ser Gln Val Val Ala Arg Glu Leu Leu Gln Pro Ser Ser
            100                 105                 110

Thr Leu Asp Ile Pro Glu Arg Leu Thr Val Asn Trp Lys Val Arg Ala
        115                 120                 125
```

-continued

```
Phe Ile Val Arg Ser His Val Pro Ala Ser Gln Pro Val Gln Val
    130                 135                 140
Leu Phe Tyr Val Ala Gly Arg Asp Trp Asp Asp Phe Gly Val Thr Glu
145                 150                 155                 160
Arg Leu Pro Cys Val Arg Leu His Ala Phe Arg Asp Ala Arg Glu Val
                165                 170                 175
Lys Ser Ser Cys Arg Leu Ser Gly Gly Leu Ala Thr Cys Leu Val Arg
            180                 185                 190
Ala Glu Leu Pro Leu Ala Trp Phe Gly Pro Ala Pro Ala Ala Pro
        195                 200                 205
Pro Thr Ala Arg Arg Lys Ser Pro Asp Gly Leu Glu Pro Glu Ala Thr
    210                 215                 220
Gly Glu Ser Gln Gln Ala Glu Leu Tyr Tyr Thr Leu His Ala Pro Asp
225                 230                 235                 240
Ala Ser Gly Gly Cys Gly Gly Ser Arg Arg Gly Ala Gly Pro Gly Val
                245                 250                 255
Gly Ala Arg Ala Glu Ser Pro Thr Gln His Pro Leu Leu Arg Ile Gly
            260                 265                 270
Ser Ile Ser Leu Phe Arg Pro Pro Arg Arg Thr Leu Gln Glu His
        275                 280                 285
Arg Leu Asp Ser Asn Leu Met Ile Arg Leu Pro Asp Arg Pro Leu Lys
    290                 295                 300
Pro Gly Glu Val Leu Ser Ile Leu Leu Tyr Leu Ala Pro Asn Ser Ser
305                 310                 315                 320
Ser Pro Ser Ser Pro Ser Val Glu His Phe Thr Leu Arg Val Lys Ala
                325                 330                 335
Lys Lys Gly Val Thr Leu Leu Gly Thr Lys Ser Arg Ser Gly Gln Trp
            340                 345                 350
His Val Thr Ser Glu Leu Leu Thr Gly Ala Lys His Ser Thr Ala Thr
        355                 360                 365
Val Asp Val Ala Trp Ala Gln Ser Thr Pro Leu Pro Pro Arg Glu Gly
    370                 375                 380
Gln Gly Pro Leu Glu Ile Leu Gln Leu Asp Phe Glu Met Glu Asn Phe
385                 390                 395                 400
Thr Ser Gln Ser Val Lys Arg Arg Ile Met Trp His Ile Asp Tyr Arg
                405                 410                 415
Gly His Gly Ala Leu Pro Asp Leu Glu Arg Ala Val Thr Glu Leu Thr
            420                 425                 430
Val Ile Gln Arg Asp Val Gln Ala Ile Leu Pro Leu Ala Met Asp Thr
        435                 440                 445
Glu Ile Ile Asn Thr Ala Ile Leu Thr Gly Arg Thr Val Ala Ile Pro
    450                 455                 460
Val Lys Val Ile Ala Ile Glu Val Asn Gly Leu Val Leu Asp Ile Ser
465                 470                 475                 480
Ala Leu Val Glu Cys Glu Ser Asp Asn Glu Asp Ile Ile Lys Val Ser
                485                 490                 495
Ser Ser Cys Asp Tyr Val Phe Val Ser Gly Lys Glu Ser Arg Gly Ser
            500                 505                 510
Met Asn Ala Arg Val Thr Phe Arg Tyr Asp Val Leu Asn Ala Pro Leu
        515                 520                 525
Glu Met Thr Val Trp Val Pro Lys Leu Pro Leu His Ile Glu Leu Ser
    530                 535                 540
```

```
Asp Ala Arg Leu Ser Gln Val Lys Gly Trp Arg Val Pro Ile Leu Pro
545                 550                 555                 560

Asp Arg Arg Ser Val Arg Glu Ser Glu Asp Glu Asp Glu Glu Glu Glu
            565                 570                 575

Glu Arg Arg Gln Ser Ala Ser Arg Gly Cys Thr Leu Gln Tyr Gln His
        580                 585                 590

Ala Thr Leu Gln Val Phe Thr Gln Phe His Thr Thr Ser Ser Glu Gly
    595                 600                 605

Thr Asp Gln Val Val Thr Met Leu Gly Pro Asp Trp Leu Val Glu Val
610                 615                 620

Thr Asp Leu Val Ser Asp Phe Met Arg Val Gly Asp Pro Arg Val Ala
625                 630                 635                 640

His Met Val Asp Ser Ser Thr Leu Ala Gly Leu Glu Pro Gly Thr Thr
                645                 650                 655

Pro Phe Lys Val Val Ser Pro Leu Thr Glu Ala Val Leu Gly Glu Thr
                660                 665                 670

Leu Leu Thr Val Thr Glu Glu Lys Val Ser Ile Thr Gln Leu Gln Ala
        675                 680                 685

Gln Val Val Ala Ser Leu Ala Leu Ser Leu Arg Pro Ser Pro Gly Ser
    690                 695                 700

Ser His Thr Ile Leu Ala Thr Ala Ala Gln Gln Thr Leu Ser Phe
705                 710                 715                 720

Leu Lys Gln Glu Ala Leu Leu Ser Leu Trp Leu Ser Tyr Ser Asp Gly
                725                 730                 735

Thr Thr Ala Pro Leu Ser Leu Tyr Ser Pro Arg Asp Tyr Gly Leu Leu
                740                 745                 750

Val Ser Ser Leu Asp Glu His Val Ala Thr Val Thr Gln Asp Arg Ala
        755                 760                 765

Phe Pro Leu Val Val Ala Glu Ala Glu Gly Ser Gly Glu Leu Leu Arg
    770                 775                 780

Ala Glu Leu Thr Ile Ala Glu Ser Cys Gln Lys Thr Lys Arg Lys Ser
785                 790                 795                 800

Val Leu Ala Thr Thr Pro Val Gly Leu Arg Val His Phe Gly Arg Asp
                805                 810                 815

Glu Glu Asp Pro Thr Tyr Asp Tyr Pro Gly Pro Ser Gln Pro Gly Pro
                820                 825                 830

Gly Gly Gly Glu Asp Glu Ala Arg Gly Ala Gly Pro Pro Gly Ser Ala
        835                 840                 845

Leu Pro Ala Pro Glu Ala Pro Gly Pro Gly Thr Ala Ser Pro Val Val
    850                 855                 860

Pro Pro Thr Glu Asp Phe Leu Pro Leu Pro Thr Gly Phe Leu Gln Val
865                 870                 875                 880

Pro Arg Gly Leu Thr Asp Leu Glu Ile Gly Met Tyr Ala Leu Leu Gly
                885                 890                 895

Val Phe Cys Leu Ala Ile Leu Val Phe Leu Ile Asn Cys Ile Val Phe
                900                 905                 910

Val Leu Arg Tyr Arg His Lys Arg Ile Pro Pro Glu Gly Gln Thr Ser
        915                 920                 925

Met Asp His Ser His His Trp Val Phe Leu Gly Asn Gly Gln Pro Leu
    930                 935                 940

Arg Val Gln Gly Glu Leu Ser Pro Pro Ala Gly Asn Pro Leu Glu Thr
945                 950                 955                 960

Val Pro Ala Phe Cys His Gly Asp His His Ser Ser Gly Ser Ser Gln
```

```
                        965                 970                 975
        Thr Ser Val Gln Ser Gln Val His Gly Arg Gly Asp Gly Ser Ser Gly
                        980                 985                 990

Gly Ser Ala Arg Asp Gln Ala Glu Asp Pro Ala Ser Ser Pro Thr Ser
                        995                1000                1005

Lys Arg Lys Arg Val Lys Phe Thr Thr Phe Thr Thr Leu Pro Ser
                1010                1015                1020

Glu Glu Leu Ala Tyr Asp Ser Val Pro Ala Gly Glu Glu Asp Glu
                1025                1030                1035

Glu Glu Glu Glu Asp Leu Gly Trp Gly Cys Pro Asp Val Ala Gly
                1040                1045                1050

Pro Thr Arg Pro Thr Ala Pro Pro Asp Leu His Asn Tyr Met Arg
                1055                1060                1065

Arg Ile Lys Glu Ile Ala
                1070

<210> SEQ ID NO 9
<211> LENGTH: 134
<212> TYPE: PRT
<213> ORGANISM: Homo sapiens

<400> SEQUENCE: 9

Met Thr Glu Glu Pro Ile Lys Glu Ile Leu Gly Ala Pro Lys Ala His
1               5                   10                  15

Met Ala Ala Thr Met Glu Lys Ser Pro Lys Ser Glu Val Val Ile Thr
            20                  25                  30

Thr Val Pro Leu Val Ser Glu Ile Gln Leu Met Ala Ala Thr Gly Gly
        35                  40                  45

Thr Glu Leu Ser Cys Tyr Arg Cys Ile Ile Pro Phe Ala Val Val Val
    50                  55                  60

Phe Ile Ala Gly Ile Val Val Thr Ala Val Ala Tyr Ser Phe Asn Ser
65                  70                  75                  80

His Gly Ser Ile Ile Ser Ile Phe Gly Leu Val Val Leu Ser Ser Gly
                85                  90                  95

Leu Phe Leu Leu Ala Ser Ser Ala Leu Cys Trp Lys Val Arg Gln Arg
            100                 105                 110

Ser Lys Lys Ala Lys Arg Arg Glu Ser Gln Thr Ala Leu Val Ala Asn
        115                 120                 125

Gln Arg Ser Leu Phe Ala
    130

<210> SEQ ID NO 10
<211> LENGTH: 281
<212> TYPE: PRT
<213> ORGANISM: Homo sapiens

<400> SEQUENCE: 10

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
```

```
                65                  70                  75                  80
Lys Trp Gln Leu Arg Gln Leu Val Arg Lys Met Ile Leu Arg Thr Ser
                    85                  90                  95
Glu Glu Thr Ile Ser Thr Val Gln Glu Lys Gln Gln Asn Ile Ser Pro
                    100                 105                 110
Leu Val Arg Glu Arg Gly Pro Gln Arg Val Ala Ala His Ile Thr Gly
                    115                 120                 125
Thr Arg Gly Arg Ser Asn Thr Leu Ser Ser Pro Asn Ser Lys Asn Glu
                    130                 135                 140
Lys Ala Leu Gly Arg Lys Ile Asn Ser Trp Glu Ser Ser Arg Ser Gly
145                 150                 155                 160
His Ser Phe Leu Ser Asn Leu His Leu Arg Asn Gly Glu Leu Val Ile
                    165                 170                 175
His Glu Lys Gly Phe Tyr Tyr Ile Tyr Ser Gln Thr Tyr Phe Arg Phe
                    180                 185                 190
Gln Glu Glu Ile Lys Glu Asn Thr Lys Asn Asp Lys Gln Met Val Gln
                    195                 200                 205
Tyr Ile Tyr Lys Tyr Thr Ser Tyr Pro Asp Pro Ile Leu Leu Met Lys
    210                 215                 220
Ser Ala Arg Asn Ser Cys Trp Ser Lys Asp Ala Glu Tyr Gly Leu Tyr
225                 230                 235                 240
Ser Ile Tyr Gln Gly Gly Ile Phe Glu Leu Lys Glu Asn Asp Arg Ile
                    245                 250                 255
Phe Val Ser Val Thr Asn Glu His Leu Ile Asp Met Asp His Glu Ala
                    260                 265                 270
Ser Phe Phe Gly Ala Phe Leu Val Gly
    275                 280
```

EXPRESSION SYSTEMS AND METHODS OF USE THEREOF

CROSS-REFERENCE TO RELATED APPLICATIONS

This application claims priority to U.S. Patent Application No. 62/849,653, filed on May 17, 2019, which is incorporated herein in its entirety.

FIELD OF THE INVENTION

This invention relates to expression systems for the expression of α9α10 nicotinic acetylcholine receptor (nAChR) and methods of use thereof.

REFERENCE TO SEQUENCE LISTING SUBMITTED ELECTRONICALLY

This application contains a sequence listing, which is submitted electronically via EFS-Web as an ASCII formatted sequence listing with a file name "PRD4024USNP1_SL.txt" and a creation date of Apr. 23, 2020 and having a size of 55,749 bytes. The sequence listing submitted via EFS-Web is part of the specification and is herein incorporated by reference in its entirety.

BACKGROUND OF THE INVENTION

Nicotinic acetylcholine receptors (nAChRs) are receptor polypeptides that respond to the neurotransmitter acetylcholine. nAChRs are pentameric ligand-gated ion channels composed of α (α1-α10) and non-α (β1-β4, ε, γ, and δ) subunits formed symmetrically around a central pore. The subunits form either homomeric channels or hetoromeric channels consisting of a combination of subunits.

The α9α10 nAChR is a heteromeric receptor formed from α9 and α10 subunits. Although α9 and α10 are members of the nicotinic family based on gene homology, nicotine is an antagonist of α9 and α9α10 nAChRs. The nAChR α9 and/or α10 subunits are expressed within hair cells of the inner ear (Elgoyhen et al. (1994) Cell 79:705-715), sperm (Kumar and Meizel (2005) J Biol Chem 280:25928-25935), dorsal root ganglion neurons (Lips et al. (2002) Neuroscience 115:1-5), skin keratinocytes (Arredondo et al. (2002) J Cell Biol 159:325-336), the pars tuberalis of the pituitary (Sgard et al. (2002) Mol Pharmacol 61:150-159), and lymphocytes (Peng et al. (2004) Life Sci 76:263-280). The α9α10 nAChRs have been suggested to have critical roles in auditory processing and neuropathic pain (Elgoyhen et al. (2001) Proc Natl Acad Sci USA. 98(6):3501-6; Vincler et al. (2006) Proc Natl Acad Sci USA. 103(47): 17880-4).

To study the pharmacological properties of nAChRs and identify receptor agonists and antagonists, heterologous expression systems are often used. However, there have been no reports to date of successful functional expression of human α9α10-containing receptors in mammalian cell lines (Lansdell et al., (2005) Mol Pharmacol. 68(5):1431-8). Thus, it is desirable to obtain an expression system that promotes functional expression of human α9α10 nAChR for high-throughput screening of regulators for discovery of potential therapeutics.

BRIEF SUMMARY OF THE INVENTION

In one general aspect provided herein are expression systems for the expression of α9α10 nicotinic acetylcholine receptor (nAChR) in mammalian cells. In certain embodiments, the expression system comprises a recombinant cell comprising (i) a first nucleic acid encoding an α9 subunit of an α9α10 nicotinic acetylcholine receptor (nAChR); (ii) a second nucleic acid encoding an α10 subunit of an α9α10 nAChR; and (iii) a third nucleic acid encoding at least one protein selected from the group consisting of Choline O-acetyltransferase (CHAT), Transmembrane inner ear expressed protein (TMIE), Transmembrane protein 132A (TMEM132A), Transmembrane protein 132C (TMEM132C), Transmembrane protein 132D (TMEM132D), Transmembrane protein 132E (TMEM132E), Transmembrane protein 100 (TMEM100) and Tumor necrosis factor receptor superfamily member 10A (TNFRSF10A).

In certain embodiments, the α9 subunit of the α9α10 nAChR comprises an amino acid sequence with at least 95% identity to the amino acid sequence of SEQ ID NO:1. In certain embodiments, the α10 subunit of the α9α10 nAChR comprises an amino acid sequence with at least 95% identity to the amino acid sequence of SEQ ID NO:2. In certain embodiments the third nucleic acid encodes CHAT. The CHAT can, for example, comprise an amino acid sequence with at least 95% identity to the amino acid sequence of SEQ ID NO:3.

In certain embodiments, the recombinant cell further comprises a fourth nucleic acid encoding at least one protein selected from the group consisting of TMIE, TMEM132A, TMEM132C, TMEM132D, TMEM132E, TMEM100 and TNFRSF10A. In certain embodiments, the fourth nucleic acid encodes TMIE. The TMIE can, for example, comprise an amino acid sequence with at least 95% identity to the amino acid sequence of SEQ ID NO:4. In certain embodiments, the fourth nucleic acid encodes TMEM132A. The TMEM132A can, for example, comprise an amino acid sequence with at least 95% identity to the amino acid sequence of SEQ ID NO5. In certain embodiments, the fourth nucleic acid encodes TMEM132C. The TMEM132C can, for example, comprise an amino acid sequence with at least 95% identity to the amino acid sequence of SEQ ID NO6. In certain embodiments, the fourth nucleic acid encodes TMEM132D. The TMEM132D can, for example, comprise an amino acid sequence with at least 95% identity to the amino acid sequence of SEQ ID NO7. In certain embodiments, the fourth nucleic acid encodes TMEM132E. The TMEM132E can, for example, comprise an amino acid sequence with at least 95% identity to the amino acid sequence of SEQ ID NO8. In certain embodiments the fourth nucleic acid encodes TMEM100. The TMEM100 can, for example, comprise an amino acid sequence with at least 95% identity to the amino acid sequence of SEQ ID NO:9. In certain embodiments, the fourth nucleic acid encodes TNFRSF10A. The TNFRSF10A can, for example, comprise an amino acid sequence with at least 95% identity to the amino acid sequence of SEQ ID NO:10.

In certain embodiments, the expression system comprises a recombinant cell comprising (i) a first nucleic acid encoding an α9 subunit of an α9α10 nicotinic acetylcholine receptor (nAChR); (ii) a second nucleic acid encoding an α10 subunit of an α9α10 nAChR; and (iii) a third nucleic acid encoding at least one protein selected from the group consisting of a Choline O-acetyltransferase (CHAT), a Transmembrane inner ear expressed protein (TMIE), a Transmembrane protein 132A (TMEM132A), a Transmembrane protein 132C (TMEM132C), a Transmembrane protein 132D (TMEM132D), a Transmembrane protein 132E (TMEM132E), a Transmembrane protein 100 (TMEM100)

and a Tumor necrosis factor receptor superfamily member 10A (TNFRSF10A); wherein the recombinant cell is cultured in media comprising at least one compound selected from acetylcholine (ACh) or methyllycaconitine (MLA).

In certain embodiments, the α9 subunit of the α9α10 nAChR comprises an amino acid sequence with at least 95% identity to the amino acid sequence of SEQ ID NO: 1. In certain embodiments, the α10 subunit of the α9α10 nAChR comprises an amino acid sequence with at least 95% identity to the amino acid sequence of SEQ ID NO: 2. In certain embodiments, the third nucleic acid encodes TMIE. In certain embodiments, the TMIE comprises an amino acid sequence with at least 95% identity to the amino acid sequence of SEQ ID NO:4.

In certain embodiments, the recombinant cell further comprises a fourth nucleic acid encoding at least one protein selected from the group consisting of CHAT, TMEM132D, TMEM100 and TNFRSF10A. In certain embodiments, the CHAT comprises an amino acid sequence with at least 95% identity to the amino acid sequence of SEQ ID NO:3, the TMEM132A comprises an amino acid sequence with at least 95% identity to the amino acid sequence of SEQ ID NO:5, the TMEM132C comprises an amino acid sequence with at least 95% identity to the amino acid sequence of SEQ ID NO:6, the TMEM132D comprises an amino acid sequence with at least 95% identity to the amino acid sequence of SEQ ID NO:7, the TMEM132E comprises an amino acid sequence with at least 95% identity to the amino acid sequence of SEQ ID NO:8, the TMEM100 comprises an amino acid sequence with at least 95% to the amino acid sequence of SEQ ID NO:9, and the TNFRSF10A comprises an amino acid sequence with at least 95% identity to the amino acid sequence of SEQ ID NO:10.

In certain embodiments, the recombinant cell is a mammalian cell. The mammalian cell can, for example, be selected from the group consisting of a human embryonic kidney 293T (HEK293T) cell, a HEK293F cell, a HeLa cell, a Chinese hamster ovary (CHO) cell, a NIH 3T3 cell, a MCF-7 cell, a Hep G2 cell, a baby hamster kidney (BHK) cell, and a Cos7 cell.

Also provided are methods of identifying agonists, antagonists, or positive allosteric modulators of an α9α10 nAChR. In certain embodiments the method comprises (a) culturing the recombinant cell of the expression systems of the invention under conditions where the recombinant cell grows; (b) contacting the recombinant cell with an agent; and (c) determining if the agent is an agonist, antagonist, or positive allosteric modulator of the α9α10 nAChR, wherein an agonist or allosteric modulator increases the activity of the α9α10 nAChR and an antagonist decreases the activity of the α9α10 nAChR as compared to the activity of the α9α10 nAChR in a recombinant cell that was not contacted with an agent. In certain embodiment the agent is a small molecule or peptide.

Also provided are methods of identifying proteins capable of enhancing expression of an α9α10 nicotinic acetylcholine receptor (nAChR). In certain embodiments, the method comprises (a) culturing a recombinant cell comprising a first nucleic acid encoding an α9 subunit of an α9α10 nicotinic acetylcholine receptor (nAChR) and a second nucleic acid encoding an α10 subunit of an α9α10 nAChR; (b) contacting the recombinant cell with a protein expression library; and (c) determining the level of expression of α9α10 nAChR, wherein an increase in α9α10 nAChR expression as compared to α9α10 expression in an uncontacted recombinant cell indicates that the protein enhances expression of α9α10 nAChR.

Also provided are kits comprising (i) the expression systems of the invention; and (ii) instructions for use.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

FIG. 2A shows a graph demonstrating the results of HEK293T cells co-transfected with α9α10 nAChR and CHAT. FIG. 2B shows a graph demonstrating the results of HEK293T cells co-transfected with α9α10 nAChR and TMIE. FIG. 2C shows a graph demonstrating the results of HEK293T cells co-transfected with α9α10 nAChR, TMIE and CHAT. Maximal FLIPR responses to ACh are plotted.

FIG. 3A shows a graph demonstrating the results of HEK293T cells co-transfected with α9α10 nAChR and CHAT. FIG. 3B shows a graph demonstrating the results of HEK293T cells co-transfected with α9α10 nAChR and TMIE. FIG. 3C shows a graph demonstrating the results of HEK293T cells co-transfected with α9α10 nAChR, TMIE and CHAT.

DETAILED DESCRIPTION OF THE INVENTION

Figure 1:
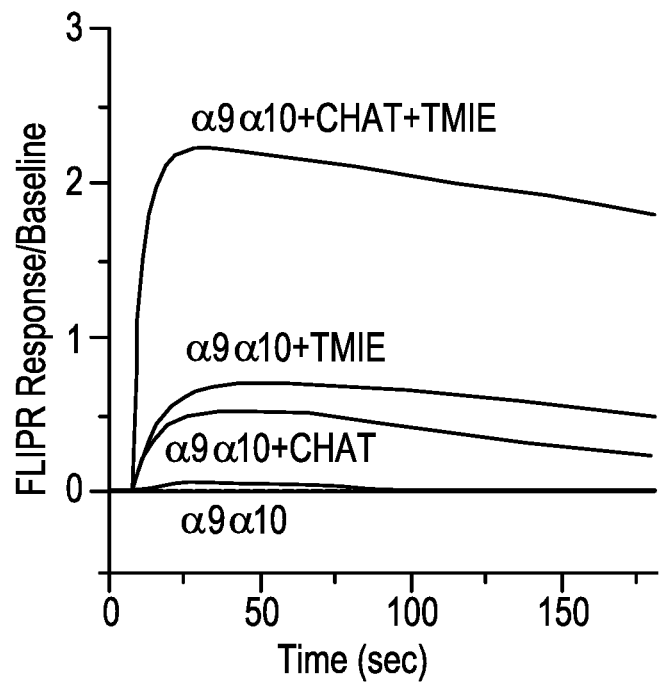
FIG. 1 shows a graph of representative Fluorescent Imaging Plate Reader (FLIPR) traces from HEK293T cells transfected with α9α10 nicotinic acetylcholine receptor (nAChR) alone, α9α10 nAChR and CHAT, α9α10 nAChR and TMIE, or α9α10 nAChR, CHAT and TMIE. Responses were evoked by treating the cells with 200 μM acetylcholine (ACh) for 180 seconds.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of" or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. § 2111.03.

It should also be understood that the terms "about," "approximately," "generally," "substantially," and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1997) Nucleic Acids Res. 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1992)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

As used herein, the term "polynucleotide," synonymously referred to as "nucleic acid molecule," "nucleotides" or "nucleic acids," refers to any polyribonucleotide or polydeoxyribonucleotide, which can be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

As used herein, the terms "peptide," "polypeptide," or "protein" can refer to a molecule comprised of amino acids and can be recognized as a protein by those of skill in the art. The conventional one-letter or three-letter code for amino acid residues is used herein. The terms "peptide," "polypeptide," and "protein" can be used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

The peptide sequences described herein are written according to the usual convention whereby the N-terminal region of the peptide is on the left and the C-terminal region is on the right. Although isomeric forms of the amino acids are known, it is the L-form of the amino acid that is represented unless otherwise expressly indicated.

Expression Systems

The invention generally relates to expression systems for the expression of α9α10 nicotinic acetylcholine receptor (nAChR) in cells. Methods of using the expression systems and kits comprising the expression systems are also provided.

As used herein, the terms "α9α10 nAChR" and "alpha9alpha10 nAChR" are used interchangeably and refer to the α9α10 nicotinic acetylcholine receptor protein, preferably the human α9α10 nAChR, which is a member of a protein family of cholinergic receptors. α9α10 nAChR is a pentameric ligand-gated ion channel composed of alpha9 and alpha10 subunits. The alpha9 subunit is encoded by the gene CHRNA9 (NM_017581) and the alpha10 subunit is encoded by the gene CHRNA10 (NM_020402). When expressed together, the subunits co-assemble to form a heteromeric nAChR (Sgard et al. (2002) Mol Pharmacol. 61(1):150-9).

The term "expression" as used herein, refers to the biosynthesis of a gene product. The term encompasses the transcription of a gene into RNA. The term also encompasses translation of RNA into one or more polypeptides, and further encompasses all naturally occurring post-transcriptional and post-translational modifications.

In a general aspect, the invention relates to expression systems comprising a recombinant cell comprising a first nucleic acid encoding an α9 subunit of an α9α10 nicotinic acetylcholine receptor (nAChR), a second nucleic acid encoding an α10 subunit of an α9α10 nAChR, and a third nucleic acid encoding at least one protein selected from the group consisting of Choline O-acetyltransferase (CHAT), Transmembrane inner ear expressed protein (TMIE), Transmembrane protein 132A (TMEM132A), Transmembrane protein 132C (TMEM132C), Transmembrane protein 132D (TMEM132D), Transmembrane protein 132E (TMEM132E), Transmembrane protein 100 (TMEM100) and Tumor necrosis factor receptor superfamily member 10A (TNFRSF10A).

In another general aspect, the invention relates to expression systems comprising a recombinant cell comprising a first nucleic acid encoding an α9 subunit of an α9α10 nicotinic acetylcholine receptor (nAChR), a second nucleic acid encoding an α10 subunit of an α9α10 nAChR, and a third nucleic acid encoding at least one peptide selected from the group consisting of a Choline O-acetyltransferase (CHAT), a Transmembrane inner ear expressed protein (TMIE), a Transmembrane protein 132A (TMEM132A), a Transmembrane protein 132C (TMEM132C), a Transmembrane protein 132D (TMEM132D), a Transmembrane protein 132E (TMEM132E), a Transmembrane protein 100 (TMEM100) and a Tumor necrosis factor receptor superfamily member 10A (TNFRSF10A), wherein the recombinant cell is cultured in media comprising at least one compound selected from acetylcholine (ACh), methyllycaconitine (MLA), choline, or nicotine.

In certain embodiments, the invention relates to an expression system comprising a recombinant cell comprising a first nucleic acid encoding an α9 subunit of an α9α10 nAChR. The α9 subunit of the α9α10 nAChR can, for example, comprise an amino acid sequence with at least 85%, preferably 90%, more preferably 95% or more, such as 95%, 96%, 97%, 98%, or 99% identity to the amino acid sequence of SEQ ID NO:1. In certain embodiments, the invention relates to an expression system comprising a recombinant cell comprising a second nucleic acid encoding an α10 subunit of an α9α10 nAChR. The α10 subunit of the α9α10 nAChR can, for example, comprise an amino acid sequence with at least 85%, preferably 90%, more preferably 95% or more, such as 95%, 96%, 97%, 98%, or 99% identity to the amino acid sequence of SEQ ID NO:2.

In certain embodiments, the invention relates to an expression system comprising a recombinant cell comprising a third nucleic acid encoding at least one peptide selected from the group consisting of Choline O-acetyltransferase (CHAT), Transmembrane inner ear expressed protein (TMIE), Transmembrane protein 132A (TMEM132A), Transmembrane protein 132C (TMEM132C), Transmembrane protein 132D (TMEM132D), Transmembrane protein 132E (TMEM132E), Transmembrane protein 100 (TMEM100) and Tumor necrosis factor receptor superfamily member 10A (TNFRSF10A).

In a particular embodiment, the third nucleic acid encodes CHAT. The CHAT can, for example, comprise an amino acid sequence with at least 85%, preferably 90%, more preferably 95% or more, such as 95%, 96%, 97%, 98%, or 99% identity to the amino acid sequence of SEQ ID NO:3.

In certain embodiments the invention relates to an expression system comprising a recombinant cell comprising a fourth nucleic acid encoding at least one peptide selected from the group consisting of TMIE, TMEM132A, TMEM132C, TMEM132D, TMEM132E, TMEM100 and TNFRSF10A. In a particular embodiment, the fourth nucleic acid encodes TMIE. The TMIE can, for example, comprise an amino acid sequence with at least 85%, preferably 90%, more preferably 95% or more, such as 95%, 96%, 97%, 98%, or 99% identity to the amino acid sequence of SEQ ID NO:4. In another embodiment, the fourth nucleic acid encodes TMEM132A. The TMEM132A can, for example, comprise an amino acid sequence with at least 85%, preferably 90%, more preferably 95% or more, such as 95%, 96%, 97%, 98%, or 99% identity to the amino acid sequence of SEQ ID NO:5. In another embodiment, the fourth nucleic acid encodes TMEM132C. The TMEM132C can, for example, comprise an amino acid sequence with at least 85%, preferably 90%, more preferably 95% or more, such as 95%, 96%, 97%, 98%, or 99% identity to the amino acid sequence of SEQ ID NO:6. In another embodiment, the fourth nucleic acid encodes TMEM132D. The TMEM132D can, for example, comprise an amino acid sequence with at least 85%, preferably 90%, more preferably 95% or more, such as 95%, 96%, 97%, 98%, or 99% identity to the amino acid sequence of SEQ ID NO:7. In another embodiment, the fourth nucleic acid encodes TMEM132E. The TMEM132E can, for example, comprise an amino acid sequence with at least 85%, preferably 90%, more preferably 95% or more, such as 95%, 96%, 97%, 98%, or 99% identity to the amino acid sequence of SEQ ID NO:8. In another embodiment, the fourth nucleic acid encodes TMEM100. The TMEM100 can, for example, comprise an amino acid sequence with at least 85%, preferably 90%, more preferably 95% or more, such as 95%, 96%, 97%, 98%, or 99% to the amino acid sequence of SEQ ID NO:9. In another embodiment, the fourth nucleic acid encodes TNFRSF10A. The TNFRSF10A can, for example, comprise an amino acid sequence with at least 85%, preferably 90%, more preferably 95% or more, such as 95%, 96%, 97%, 98%, or 99% identity to the amino acid sequence of SEQ ID NO:10.

In a general aspect, the invention relates to expression systems comprising a recombinant cell. Any cell known to those skilled in the art in view of the present disclosure can be used for recombinant expression of α9α10 nAChR. According to certain embodiments, the recombinant cell is a mammalian cell. In particular embodiments, the mammalian cell is selected from the group consisting of a human embryonic kidney 293T (HEK293T) cell, a HEK293F cell, a HeLa cell, a Chinese hamster ovary (CHO) cell, a NIH 3T3 cell, a MCF-7 cell, a Hep G2 cell, a baby hamster kidney (BHK) cell, and a Cos7 cell.

The nucleic acids of the invention can, for example, be comprised in a vector. Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible or repressible promoter. A number of expression vectors capable of delivering nucleic acids to a cell are known in the art and can be used herein. Conventional cloning techniques or artificial gene synthesis can be used to generate a recombinant expression vector according to embodiments of the invention.

In a general aspect, the invention relates to methods of identifying agonists, antagonists, or positive allosteric modulators of an α9α10 nAChR. In certain embodiments, the method of identifying agonists, antagonists, or positive allosteric modulators of an α9α10 nAChR, the method comprising culturing a recombinant cell of the expression system of the invention under conditions where the recombinant cell grows, contacting the recombinant cell with an agent, and determining if the agent is an agonist, antagonist, or positive allosteric modulator of the α9α10 nAChR, wherein an agonist or allosteric modulator increases the activity of the α9α10 nAChR and an antagonist decreases the activity of the α9α10 nAChR as compared to the activity of the α9α10 nAChR in a recombinant cell that was not contacted with an agent. Agonists, as used herein, refer to molecules/compounds/peptides that serve to enhance the function of the α9α10 nAChR. Positive allosteric modulators, as used herein, refer to molecules/compounds/peptides that enhance the effect of α9α10 nAChR's response to a ligand without directly activating the receptor. As used herein, the term "enhance," "enhanced," "increase," or "increased," when used with respect to α9α10 nAChR activity refers to an increase in the signaling through the receptor, relative to the corresponding signaling observed in a cell in which an agonist or allosteric modulator is not administered. Antagonists, as used herein, refer to molecules/compounds/peptides that serve to block, decrease, or dampen the function of the α9α10 nAChR. In particular embodiments, the agent is a small molecule or peptide.

In a general aspect, the invention is also related to identifying peptides capable of enhancing expression of an α9α10 nicotinic acetylcholine receptor (nAChR). In certain embodiments, the method comprises culturing a recombinant cell comprising a first nucleic acid encoding an α9 subunit of an α9α10 nicotinic acetylcholine receptor (nAChR) and a second nucleic acid encoding an α10 subunit of an α9α10 nAChR; contacting the recombinant cell with a peptide expression library; and determining the level of expression of α9α10 nAChR, wherein an increase in α9α10 nAChR expression as compared to α9α10 expression in an uncontacted recombinant cell indicates that the peptide enhances expression of α9α10 nAChR.

Another particular aspect of the invention relates to kits comprising the expression systems of the invention and instructions for use.

EMBODIMENTS

This invention provides the following non-limiting embodiments.

Embodiment 1 is an expression system comprising a recombinant cell comprising
(i) a first nucleic acid encoding an α9 subunit of an α9α10 nicotinic acetylcholine receptor (nAChR);
(ii) a second nucleic acid encoding an α10 subunit of an α9α10 nAChR; and
(iii) a third nucleic acid encoding at least one protein selected from the group consisting of Choline O-acetyltransferase (CHAT), Transmembrane inner ear expressed protein (TMIE), Transmembrane protein 132A (TMEM132A), Transmembrane protein 132C (TMEM132C), Transmembrane protein 132D (TMEM132D), Transmembrane protein 132E (TMEM132E), Transmembrane protein 100 (TMEM100) and Tumor necrosis factor receptor superfamily member 10A (TNFRSF10A).

Embodiment 2 is the expression system of embodiment 1, wherein the recombinant cell is a mammalian cell.

Embodiment 3 is the expression system of embodiment 2, wherein the mammalian cell is selected from the group consisting of a human embryonic kidney 293T (HEK293T) cell, a HEK293F cell, a HeLa cell, a Chinese hamster ovary (CHO) cell, a NIH 3T3 cell, a MCF-7 cell, a Hep G2 cell, a baby hamster kidney (BHK) cell, and a Cos7 cell.

Embodiment 4 is the expression system of any one of embodiments 1-3, wherein the α9 subunit of the α9α10 nAChR comprises an amino acid sequence with at least 95% identity to the amino acid sequence of SEQ ID NO:1.

Embodiment 5 is the expression system of any one of embodiments 1-4, the α10 subunit of the α9α10 nAChR comprises an amino acid sequence with at least 95% identity to the amino acid sequence of SEQ ID NO:2.

Embodiment 6 is the expression system of any one of embodiments 1-5, wherein the third nucleic acid encodes CHAT.

Embodiment 7 is the expression system of embodiment 6, wherein the CHAT comprises an amino acid sequence with at least 95% identity to the amino acid sequence of SEQ ID NO:3.

Embodiment 8 is the expression system of embodiment 7, wherein the recombinant cell further comprises a fourth nucleic acid encoding at least one protein selected from the group consisting of TMIE, TMEM132A, TMEM132C, TMEM132D, TMEM132E TMEM100 and TNFRSF10A.

Embodiment 9 is the expression system of embodiment 8, wherein the fourth nucleic acid encodes TMIE.

Embodiment 10 is the expression system of embodiment 9, wherein the TMIE comprises an amino acid sequence with at least 95% identity to the amino acid sequence of SEQ ID NO:4.

Embodiment 11 is the expression system of embodiment 8, wherein the TMEM132A comprises an amino acid sequence with at least 95% identity to the amino acid sequence of SEQ ID NO:5, the TMEM132C comprises an amino acid sequence with at least 95% identity to the amino acid sequence of SEQ ID NO:6, the TMEM132D comprises an amino acid sequence with at least 95% identity to the amino acid sequence of SEQ ID NO:7, the TMEM132E comprises an amino acid sequence with at least 95% identity to the amino acid sequence of SEQ ID NO:8, the TMEM100 comprises an amino acid sequence with at least 95% to the amino acid sequence of SEQ ID NO:9, and the TNFRSF10A comprises an amino acid sequence with at least 95% identity to the amino acid sequence of SEQ ID NO:10.

Embodiment 12 is an expression system comprising a recombinant cell comprising
(i) a first nucleic acid encoding an α9 subunit of an α9α10 nicotinic acetylcholine receptor (nAChR);
(ii) a second nucleic acid encoding an α10 subunit of an α9α10 nAChR; and
(iii) a third nucleic acid encoding at least one protein selected from the group consisting of a Choline O-acetyltransferase (CHAT), a Transmembrane inner ear expressed protein (TMIE), a Transmembrane protein 132A (TMEM132A), a Transmembrane protein 132C (TMEM132C), a Transmembrane protein 132D (TMEM132D), a Transmembrane protein 132E (TMEM132E), a Transmembrane protein 100 (TMEM100) and a Tumor necrosis factor receptor superfamily member 10A (TNFRSF10A);
wherein the recombinant cell is cultured in media comprising at least one compound selected from acetylcholine (ACh) or methyllycaconitine (MLA).

Embodiment 13 is the expression system of embodiment 12, wherein the recombinant cell is a mammalian cell.

Embodiment 14 is the expression system of embodiment 13, wherein the mammalian cell is selected from the group consisting of a human embryonic kidney 293T (HEK293T) cell, a HEK293F cell, a HeLa cell, a Chinese hamster ovary (CHO) cell, a NIH 3T3 cell, a MCF-7 cell, a Hep G2 cell, a baby hamster kidney (BHK) cell, and a Cos7 cell.

Embodiment 15 is the system expression system of any one of embodiments 12-14, wherein the α9 subunit of the α9α10 nAChR comprises an amino acid sequence with at least 95% identity to the amino acid sequence of SEQ ID NO:1.

Embodiment 16 is the expression system of any one of embodiments 12-15, wherein the α10 subunit of the α9α10 nAChR comprises an amino acid sequence with at least 95% identity to the amino acid sequence of SEQ ID NO:2.

Embodiment 17 is the expression system of any one of embodiments 12-16, wherein the third nucleic acid encodes TMIE.

Embodiment 18 is the expression system of embodiment 17, wherein the TMIE comprises an amino acid sequence with at least 95% identity to the amino acid sequence of SEQ ID NO:4.

Embodiment 19 is the expression system of embodiment 18, wherein the recombinant cell further comprises a fourth nucleic acid encoding at least one protein selected from the group consisting of CHAT, TMEM132A, TMEM132C, TMEM132D, TMEM132E, TMEM100 and TNFRSF10A.

Embodiment 20 is the expression system of embodiment 19, wherein the CHAT comprises an amino acid sequence with at least 95% identity to the amino acid sequence of SEQ ID NO:3, the TMEM132A comprises an amino acid sequence with at least 95% identity to the amino acid sequence of SEQ ID NO:5, the TMEM132C comprises an amino acid sequence with at least 95% identity to the amino acid sequence of SEQ ID NO:6, the TMEM132D comprises an amino acid sequence with at least 95% identity to the amino acid sequence of SEQ ID NO:7, the TMEM132D comprises an amino acid sequence with at least 95% identity to the amino acid sequence of SEQ ID NO:8, the TMEM100 comprises an amino acid sequence with at least 95% to the amino acid sequence of SEQ ID NO:9, and the TNFRSF10A comprises an amino acid sequence with at least 95% identity to the amino acid sequence of SEQ ID NO:10.

Embodiment 21 is a method of identifying agonists, antagonists, or positive allosteric modulators of an α9α10 nAChR, the method comprising:
 a. culturing the recombinant cell of the expression system of any one of embodiments 1-20 under conditions where the recombinant cell grows;
 b. contacting the recombinant cell with an agent; and
 c. determining if the agent is an agonist, antagonist, or positive allosteric modulator of the α9α10 nAChR, wherein an agonist or allosteric modulator increases the activity of the α9α10 nAChR and an antagonist decreases the activity of the α9α10 nAChR as compared to the activity of the α9α10 nAChR in a recombinant cell that was not contacted with an agent.

Embodiment 22 is the method of embodiment 21, wherein the agent is a small molecule or peptide.

Embodiment 23 is a method of identifying proteins capable of enhancing expression of an α9α10 nicotinic acetylcholine receptor (nAChR), the method comprising:
 a. culturing a recombinant cell comprising a first nucleic acid encoding an α9 subunit of an α9α10 nicotinic acetylcholine receptor (nAChR) and a second nucleic acid encoding an α10 subunit of an α9α10 nAChR;
 b. contacting the recombinant cell with a protein expression library; and
 c. determining the level of expression of α9α10 nAChR, wherein an increase in α9α10 nAChR expression as compared to α9α10 expression in an uncontacted recombinant cell indicates that the protein enhances expression of α9α10 nAChR.

Embodiment 24 is a kit comprising (i) the expression system of any one of embodiments 1-20; and (ii) instructions for use.

EXAMPLES

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

Example 1. High-Throughput Screening to Identify Regulators of α9α10 Nicotinic Acetylcholine Receptor (nAChR) Expression in Cells Human embryonic kidney 293T (HEK293T) cells were cultured in high glucose DMEM medium supplemented with 10% FBS, sodium pyruvate and penicillin/streptomycin. Prior to transfection, cells were seeded at ~80-90% confluence in 384-well fluorescence imaging plate reader (FLIPR) assay plates. After a 4 hour (hr) incubation, wells of cells were individually co-transfected with human α9α10 nAChR plus one of 20,000 clones from cDNA libraries encoding most all human proteins (Origene Technologies; Rockville, Md.; Broad Institute; Cambridge, Mass.) using Fugene HD (Promega; Madison, Wis.) according to the manufacture's protocol. After two days incubation, cells were washed three times with assay buffer (137 mM NaCl, 4 mM KCl, 2 mM CaCl2, 1 mM MgCl2, 5 mM glucose, 10 mM HEPES pH7.4) and loaded with Calcium5 dye (Molecular Devices; San Jose, Calif.) and 1.25 mM probenecid for 1 hr at room temperature (RT). After three washes, the plates were placed in the FLIPR stage. After establishing baseline, 200 μM acetylcholine (ACh) was applied for a 180 second recording.

From these experiments, it was found that five clones enabled functional expression of co-transfected α9α10 nAChR. These clones encoded Choline O-acetyltransferase (CHAT) (SEQ ID NO: 3), Transmembrane inner ear expressed protein (TMIE) (SEQ ID NO: 4), Transmembrane protein 132A (TMEM132A) (SEQ ID NO: 5), Transmembrane protein 132C (TMEM132C) (SEQ ID NO: 6),Transmembrane protein 132D (TMEM132D) (SEQ ID NO: 7), Transmembrane protein 132E (TMEM132E) (SEQ ID NO: 8)Transmembrane protein 100 (TMEM100) (SEQ ID NO: 9) and Tumor necrosis factor receptor superfamily member 10A (TNFRSF10A) (SEQ ID NO: 10).

TABLE 1

| SEQ ID NO: | NAME | Amino Acid Sequence |
|---|---|---|
| 1 | Alpha 9 subunit | MNWSHSCISFCWIYFAASRLRAAETADGKYAQKLFNDLFEDYSNALR PVEDTDKVLNVTLQITLSQIKDMDERNQILTAYLWIRQIWHDAYLTW DRDQYDGLDSIRIPSDLVWRPDIVLYNKADDESSEPVNTNVVLRYDG LITWDAPAITKSSCVVDVTYFPFDNQQCNLTFGSWTYNGNQVDIFNA LDSGDLSDFIEDVEWEVHGMPAVKNVISYGCCSEPYPDVTFTLLLKR RSSFYIVNLLIPCVLISFLAPLSFYLPAASGEKVSLGVTILLAMTVF QLMVAEIMPASENVPLIGKYYIATMALITASTALTIMVMNIHFCGAE ARPVPHWARVVILKYMSRVLFVYDVGESCLSPHHSRERDHLTKVYSK LPESNLKAARNKDLSRKKDMNKRLKNDLGCQGKNPQEAESYCAQYKV LTRNIEYIAKCLKDHKATNSKGSEWKKVAKVIDRFFMWIFFIMVFVM TILIIARAD |
| 2 | Alpha 10 subunit | MGLRSHHLSLGLLLLFLLPAECLGAEGRLALKLFRDLFANYTSALRP VADTDQTLNVTLEVTLSQIIDMDERNQVLTLYLWIRQEWTDAYLRWD PNAYGGLDAIRIPSSLVWRPDIVLYNKADAQPPGSASTNVVLRHDGA VRWDAPAITRSSCRVDVAAFPFDAQHCGLTFGSWTHGGHQLDVRPRG AAASLADFVENVEWRVLGMPARRRVLTYGCCSEPYPDVTFTLLLRRR AAAYVCNLLLPCVLISLLAPLAFHLPADSGEKVSLGVTVLLALTVFQ LLLAESMPPAESVPLIGKYYMATMTMVTFSTALTILIMNLHYCGPSV |

TABLE 1-continued

| SEQ ID NO: | NAME | Amino Acid Sequence |
|---|---|---|
| | | RPVPAWARALLLGHLARGLCVRERGEPCGQSRPPELSPSPQSPEGGA GPPAGPCHEPRCLCRQEALLHHVATIANTFRSHRAAQRCHEDWKRLA RVMDRFFLAIFFSMALVMSLLVLVQAL |
| 3 | CHAT | MAAKTPSSEESGLPKLPVPPLQQTLATYLQCMRHLVSEEQFRKSQAI VQQFGAPGGLGETLQQKLLERQEKTANWVSEYWLNDMYLNNRLALPV NSSPAVIFARQHFPGTDDQLRFAASLISGVLSYKALLDSHSIPTDCA KGQLSGQPLCMKQYYGLFSSYRLPGHTQDTLVAQNSSIMPEPEHVIV ACCNQFFVLDVVINFRRLSEGDLFTQLRKIVKMASNEDERLPPIGLL TSDGRSEWAEARTVLVKDSTNRDSLDMIERCICLVCLDAPGGVELSD THRALQLLHGGGYSKNGANRWYDKSLQFVVGRDGTCGVVCEHSPFDG IVLVQCTEHLLKHMTQSSRKLIRADSVSELPAPRRLRWKCSPEIQGH LASSAEKLQRIVKNLDFIVYKFDNYGKTFIKKQKCSPDAFIQVALQL AFYRLHRRLVPTYESASIRRFQEGRVDNIRSATPEALAFVRAVTDHK AAVPASEKLLLLKDAIRAQTAYTVMAITGMAIDNHLLALRELARAMC KELPEMFMDETYLMSNRFVLSTSQVPTTIEMFCCYGPVVPNGYGACY NPQPETILFCISSFHSCKETSSSKFAKAVEESLIDMRDLCSLLPPTE SKPLATKEKATRPSQGHQP |
| 4 | TMIE | MAGWPGAGPLCVLGGAALGVCLAGVAGQLVEPSTAPPKPKPPPLTKE TVVFWDMRLWHVVGIFSLFVLSIIITLCCVFNCRVPRTRKEIEARYL QRKAAKMYTDKLETVPPLNELTEVPGEDKKSVDTVAIKVEEDEKNEA KKKKGEK |
| 5 | TMEM132A | MCARMAGRTTAAPRGPYGPWLCLLVALALDVVRVDCGQAPLDPVYLP AALELLLDAPEHFRVQQVGHYPPANSSLSSRSETFLLLQPWPRAQPLL RASYPPFATQQVVPPRVTEPHQRPVPWDVRAVSVEAAVTPAEPYARV LFHLKGQDWPPGSGSLPCARLHATHPAGTAHQACRFQPSLGACVVEL ELPSHWFSQASTTRAELAYTLEPAAEGPGGCGSGEENDPGEQALPVG GVELRPADPPQYQEVPLDEAVTLRVPDMPVRPGQLFSATLLLRHNFT ASLLTLRIKVKKGLHVTAARPAQPTLWTAKLDRFKGSRHHTTLITCH RAGL1EPDSSPLELSEFLWVDFVVENSTGGGVAVTRPVTWQLEYPGQ APEAEKDKMVWEILVSERDIRALIPLAKAEELVNTAPLTGVPQHVPV RLVTVDGGGALVEVTEHVGCESANTQVLQVSEACDAVFVAGKESRGA RGVRVDFWWRRLRASLRLTVWAPLLPLRIELTDTTLEQVRGWRVPGP AEGPAEPAAEASDEAERRARGCHLQYQRAGVRFLAPFAAHPLDGGRR LTHLLGPDWLLDVSHLVAPHARVLDSRVASLEGGRVVVGREPGVTSI EVRSPLSDSILGEQALAVTDDKVSVLELRVQPVMGISLTLSRGTAHP GEVTATCWAQSALPAPKQEVALSLWLSFSDHTVAPAELYDRRDLGLS VSAEEPGAILPAEEQGAQLGVVVSGAGAEGLPLHVALHPPEPCRRGR HRVPLASGTAWLGLPPASTPAPALPSSPAWSPPATEATMGGKRQVAG SVGGNTGVRGKFERAEEEARKEE1EAREEEEEEEEEMVPAPQHVTEL ELGMYALLGVFCVAIFIFLVNGVVFVLRYQRKEPPDSATDPTSPQPH NWVWLGTDQEELSRQLDRQSPGPPKGEGSCPCESGGGGEAPTLAPGP PGGTTSSSSTLARKEAGGRRKRVEFVTFAPAPPAQSPEEPVGAPAVQ SILVAGEEDIRWVCEDMGLKDPEELRNYMERIRGSS |
| 6 | TMEM132C | MRSEGAAPGPAAPLCGALSLLLGALLGKVIEGHGVTDNIQRFSSLPP YLPVSYHILRAETSFFLKEANQDLLRNSSLQARVESFFTYKTRQPPV LNASYGPFSVEKVVPLDLMLTSNFLGPTNKFSFDWKLKAHILRDKVY LSRPKVQVLFHIMGRDWDDHGAGEKLPCLRVFAFRETREVRGSCRLK GDLGLCVAELELLSSWFSAPTVGAGRKKSMDQPEGTPVELYYTVHPG NERGDCAGGDFRKGNAIRPGKDGLEETTSHLQRIGTVGLYRAQDSAQ LSELRLDGNVVIWLPSRPVKQGEVVTAYVTISSNSSVDLFILRAKVK KGVNILSAQTREPRQWGVKQEVGSGGKHVTATVACQRLGPSPRNRSS SLFNEVVQMNFEIASFSSLSGTQPITWQVEYPRKGTTDIAVSEIFVS QKDLVGIVPLAMDTEILNTAVLTGKTVAMPIKVVSVEENSAVMDISE SVECKSTDEDVIKVSERCDYIFVNGKEIKGKMDAVVNFTYQYLSAPL CVTVWVPRLPLQIEVSDILLSQIKGWRVPIVTNKRPTRESEDEDEEE RRGRGCALQYQHATVRVLTQFVSEGAGPWGQPNYLLSPNWQFDITHL VADPMKLEEPHVATLQDSRVLVGREVGMTTIQVLSPLSDSILAEKTI TVLDDKVSVTDLAIQLVAGLSVALYPNAENSKAVTAVVTAEEVLRTP KQEAVFSTWLQFSDGSVTPLDIYDTKDFSLAATSQDEAVVSVPQPRS PRWPVVVAEGEGQGPLIRVDMTIAEACQKSKRKSILAVGVGNVRVKF GQNDADSSPGGDYEEDEIKNHASDRRQKGQHHERTGQDGHLYGSSPV EREEGALRRATTARSLLDDNKVVKNSRADGGRLAGEGQLQNIPIDFT NFPAHVDLPKAGSGLEENDLVQTPRGLSDLEIGMYALLGVFCLAILV FLINCATFALKYRHKQVPLEGQASMTHSHDWVWLGNEAELLESMGDA PPPQDEHTTIIDRGPGACEESNHLLLNGGSHKHVQSQIHRSADSGGR QGREQKQDPLHSPTSKRKKVKFTTFTTIPPDDSCPTVNSIVSSNDED IKWVCQDVAVGAPKELRNYLEKLKDKA |
| 7 | TMEM132D | MCPSEMGTLWHHWSPVLISLAALFSKVTEGRGILESIQRFSLLPTYL PVTYHINNADVSFFLKEANQDIMRNSSLQSRVESFLIYKSRRLPVLN ASYGPFSIEQVVPQDLMLPSNPFGFTNKFSLNWKLKAHILRDKVYLS |

TABLE 1-continued

| SEQ ID NO: | NAME | Amino Acid Sequence |
|---|---|---|
| | | RPKVQVLFHIMGRDWDDRSAGEKLPCLRVFAFRETREVRGSCRLQGD<br>LGLCVAELELLSSWFSPPTVVAGRRKSVDQPEGTPVELYYTVHPGGE<br>RGDCVREDARRSNGIRTGHSDIDESGPPLQRIGSIFLYQTHRKPSLR<br>ELRLDNSVAIHYIPKTVRKGDVLTFPVSISRNS1EDRFTLRAKVKKG<br>VNIIGVRASSPSIWDVKERTDYTGKYAPAVIVCQKKAAGSENSADGA<br>SYEVMQIDVEVEEPGDLPATQLVTWQVEYPGEITSDLGVSKIYVSPK<br>DLIGVVPLAMEAEILNTAILTGKTVAVPVKVVSVEDDGTVTELLESV<br>ECRSSDEDVIKVSDRCDYVFVNGKEMKGKVNVVVNFTYQHLSSPLEM<br>TVWVPRLPLQIEVSDTELNQIKGWRVPIVSSRRPAGDSEEEEDDERR<br>GRGCTLQYQHAMVRVLTQFVAEAAGPGGHLAHLLGSDWQVDI1ELIN<br>DFMQVEEPRIAKLQGGQILMGQELGMTTIQILSPLSDTILAEKTITV<br>LDEKVTITDLGVQLVTGLSLSLQLSPGSNRAIFATAVAQELLQRPKQ<br>EAAISCWVQFSDGSVTPLDIYDGKDFSLMATSLDEKVVSIHQDPKFK<br>WPIIAAE1EGQGTLVKVEMVISESCQKSKRKSVLAVGTANIKVKFGQ<br>NDANPNTSDSRHTGAGVHMENNVSDRRPKKPSQEWGSQEGQYYGSSS<br>MGLMEGRGTTTDRSILQKKKGQESLLDDNSHLQTIPSDLTSFPAQVD<br>LPRSNGEMDGNDLMQASKGLSDLEIGMYALLGVFCLAILVFLINCVT<br>FALKYRHKQVPFEEQEGMSHSHDWVGLSNRTELLENHINFASSQDEQ<br>ITAIDRGMDFEESKYLLSTNSQKSINGQLFKPLGPIIIDGKDQKSEP<br>PTSPTSKRKRVKFTTFTAVSSDDEYPTRNSIVMSSEDDIKWVCQDLD<br>PGDCKELHNYMERLHENV |
| 8 | TMEM132E | MAPGMSGRGGAALLCLSALLAHASGRSHPASPSPPGPQASPVLPVSY<br>RLSHTRLAFFLREARPPSPAVANSSLQRSEPFVVFQTKELPVLNVSL<br>GPFSTSQVVARELLQPSSTLDIPERLTVNWKVRAFIVRSHVPASQPV<br>VQVLFYVAGRDWDDFGVTERLPCVRLHAFRDAREVKSSCRLSGGLAT<br>CLVRAELPLAWFGPPAPAAPPTARRKSPDGLEPEATGESQQAELYYT<br>LHAPDASGGCGGSRRGAGPGVGARAESPTQHPLLRIGSISLFRPPPR<br>RTLQEHRLDSNLMIRLPDRPLKPGEVLSILLYLAPNSSSPSSPSVEH<br>FTLRVKAKKGVTLLGTKSRSGQWHVTSELLTGAKHSTATVDVAWAQS<br>TPLPPREGQGPLEILQLDFEMENFTSQSVKRRIMWHIDYRGHGALPD<br>LERAVTELTVIQRDVQAILPLAMD1EIINTAILTGRTVAIPVKVIAI<br>EVNGLVLDISALVECESDNEDIIKVSSSCDYVFVSGKESRGSMNARV<br>TFRYDVLNAPLEMTVWVPKLPLHIELSDARLSQVKGWRVPILPDRRS<br>VRESEDEDEEEEERRQSASRGCTLQYQHATLQVFTQFHTTSSEGTDQ<br>VVTMLGPDWLVEVTDLVSDFMRVGDPRVAHMVDSSTLAGLEPGTTPF<br>KVVSPL1EAVLGETLLTVTEEKVSITQLQAQVVASLALSLRPSPGSS<br>HTILATTAAQQTLSFLKQEALLSLWLSYSDGTTAPLSLYSPRDYGLL<br>VSSLDEHVATVTQDRAFPLVVAEAEGSGELLRAELTIAESCQKTKRK<br>SVLATTPVGLRVHFGRDEEDPTYDYPGPSQPGPGGGEDEARGAGPPG<br>SALPAPEAPGPGTASPVVPPTEDFLPLPTGFLQVPRGLTDLEIGMYA<br>LLGVFCLAILVFLINCIVFVLRYRHKRIPPEGQTSMDHSHHWVFLGN<br>GQPLRVQGELSPPAGNPLETVPAFCHGDHHSSGSSQTSVQSQVHGRG<br>DGSSGGSARDQAEDPASSPTSKRKRVKFTTFTTLPSEELAYDSVPAG<br>EEDEEEEEDLGWGCPDVAGPTRPTAPPDLHNYMRRIKEIA |
| 9 | TMEM100 | MTEEPIKEILGAPKAHMAATMEKSPKSEVVITTVPLVSEIQLMAATG<br>GTELSCYRCIIPFAVVVFIAGIVVTAVAYSFNSHGSIISIFGLVVLS<br>SGLFLLASSALCWKVRQRSKKAKRRESQTALVANQRSLFA |
| 10 | TNFRSF10A | MAMMEVQGGPSLGQTCVLIVIFTVLLQSLCVAVTYVYFTNELKQMQD<br>KYSKSGIACFLKEDDSYWDPNDEESMNSPCWQVKWQLRQLVRKMILR<br>TSEETISTVQEKQQNISPLVRERGPQRVAAHITGTRGRSNTLSSPNS<br>KNEKALGRKINSWESSRSGHSFLSNLHLRNGELVIHEKGFYYIYSQT<br>YFRFQEEIKENTKNDKQMVQYIYKYTSYPDPILLMKSARNSCWSKDA<br>EYGLYSIYQGGIFELKENDRIFVSVTNEHLIDMDHEASFFGAFLVG |

To further characterize the regulation of α9α10 nAChR expression, HEK293T cells were co-transfected with α9α10 nAChR and each of CHAT, TMIE, TMEM100, TMEM132A, TMEM132C, TMEM132D, TMEM132E and TNFRSF10A individually and in combination (Table 2). In HEK293T cells transfected with α9α10 nAChR and TMIE or α9α10 nAChR and CHAT, 200 μM ACh application evoked significant FLIPR responses (FIG. 1). By contrast, transfection of α9α10 nAChR and vector DNA did not. Furthermore, expression of TMIE and CHAT proteins synergized to enhance functional responses from α9α10 nAChR (FIG. 1).

TABLE 2

| | FLIPR Response (Fold/Baseline) | |
|---|---|---|
| Gene Name | α9α10 nAChR | α9α10 nAChR + CHAT |
| Vector Control | 0 | 0.5 |
| TMIE | 0.7 | 2.2 |
| TMEM100 | 0.6 | 3.0 |
| TMEM132A | 0.3 | 2.5 |
| TMEM132C | 0.7 | 2.0 |
| TMEM132D | 0.4 | 2.6 |

TABLE 2-continued

| | FLIPR Response (Fold/Baseline) | |
|---|---|---|
| Gene Name | α9α10 nAChR | α9α10 nAChR + CHAT |
| TMEM132E | 0.7 | 2.6 |
| TNFRSF10A | 0.4 | 2.0 |

Figure 2A:
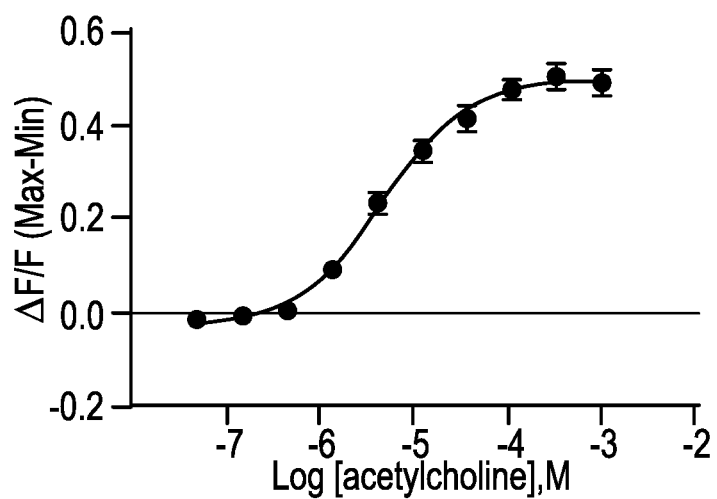
FIGS. 2A-C show graphs of FLIPR traces from HEK293T cells treated with varying concentrations of ACh for 180 seconds.
Figure 2B:
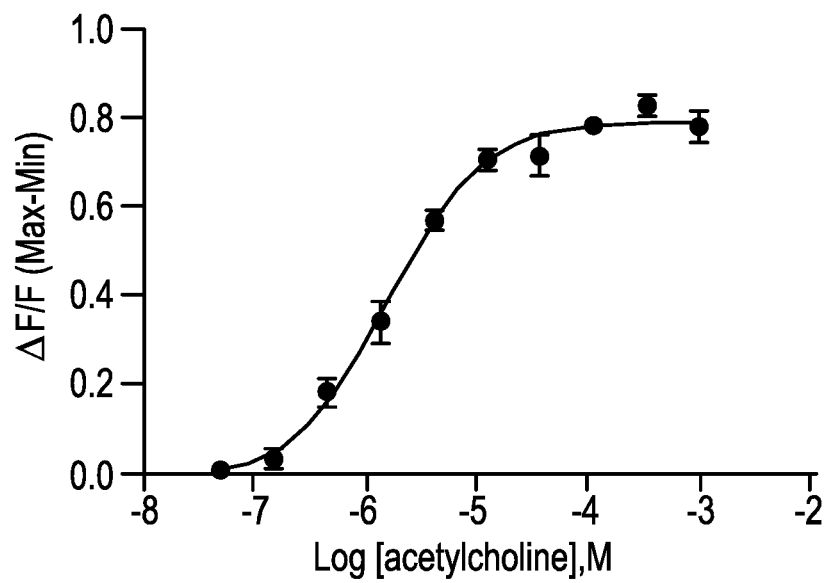
Figure 2C:
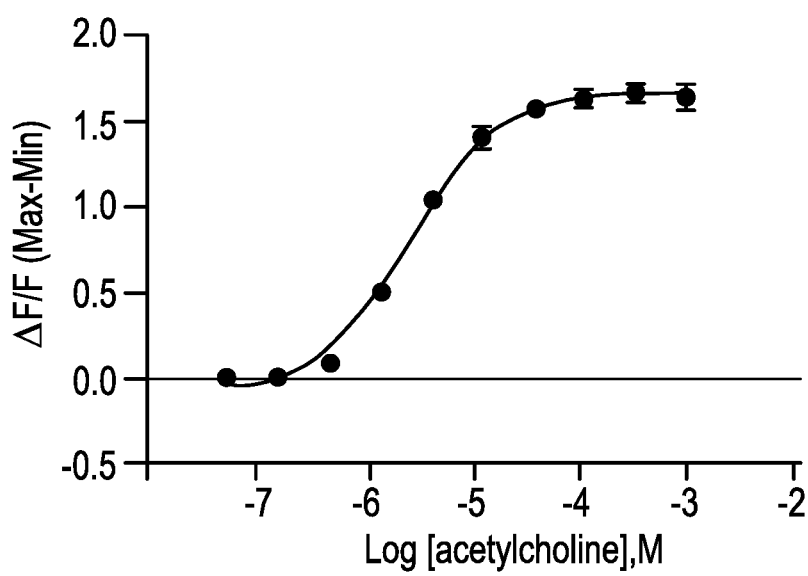

Example 2. α9α10 nAChR Dose Response to Varying Concentrations of Acetylcholine HEK293T cells were co-transfected as described in Example 1 with α9α10 nAChR and CHAT, α9α10 nAChR and TMIE, or α9α10 nAChR, CHAT and TMIE. After two days incubation, cells were washed three times with assay buffer (137 mM NaCl, 4 mM KCl, 2 mM CaCl2, 1 mM MgCl2, 5 mM glucose, 10 mM HEPES pH7.4) and loaded with Calcium5 dye and 1.25 mM probenecid for 1 hr at room temperature (RT). After three washes, the plates were placed in the FLIPR stage. After establishing baseline, varying doses of ACh was applied for a 180 second recording. Maximal FLIPR responses to ACh were plotted (FIGS. 2A-C). Consistent with the literature for α9α10 expressed in cochlear hair cells or oocytes (Elgoyhen et al., 2001), the agonist ACh has an $EC_{50}$~2-4 µM (Table 3).

TABLE 3

| Gene Name | Acetylcholine $EC_{50}$ (µM) |
|---|---|
| α9α10 nAChR + CHAT | 3.4 |
| α9α10 nAChR + TMIE | 1.3 |
| α9α10 nAChR + CHAT + TMIE | 2.5 |

Example 3. Pharmacological Characterization of α9α10 nAChR in HEK293T Cells

Figure 3A:
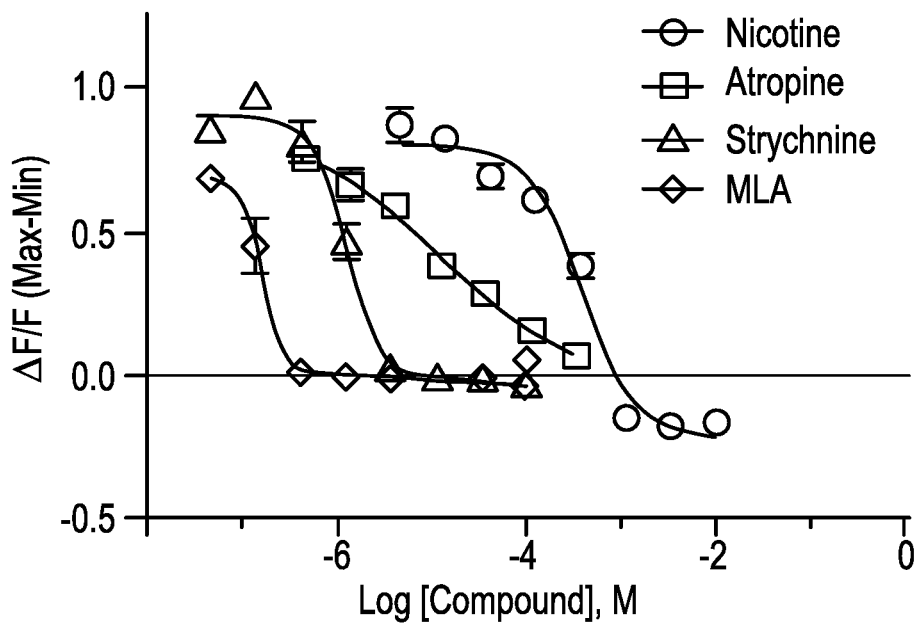
FIGS. 3A-C show graphs of FLIPR traces from HEK293T cells demonstrating pharmacological characterization of α9α10 nAChR. Responses were evoked by treating the cells with 200 μM ACh for 180 seconds in the presence of varying concentrations of antagonists.
Figure 3B:
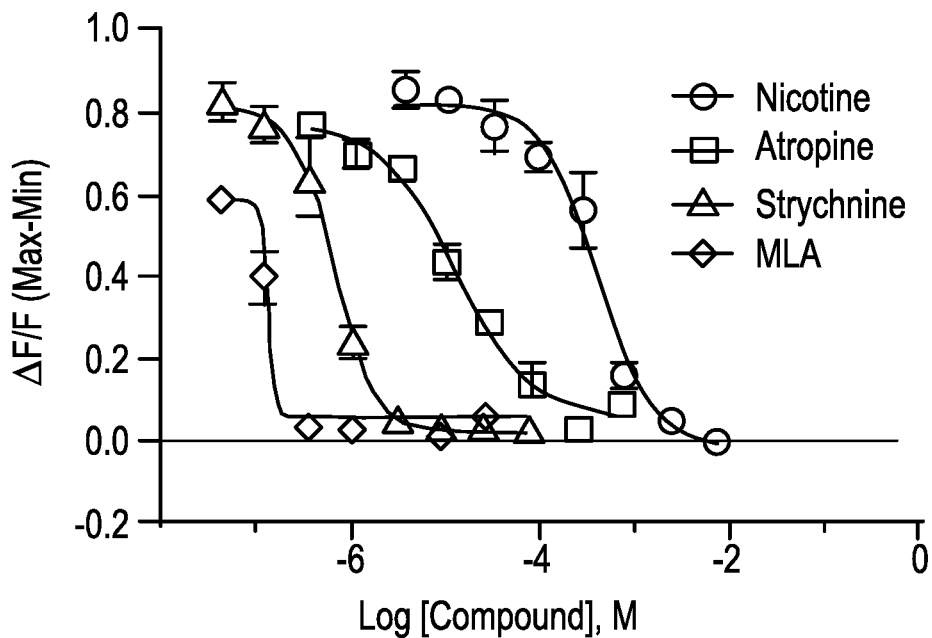
Figure 3C:
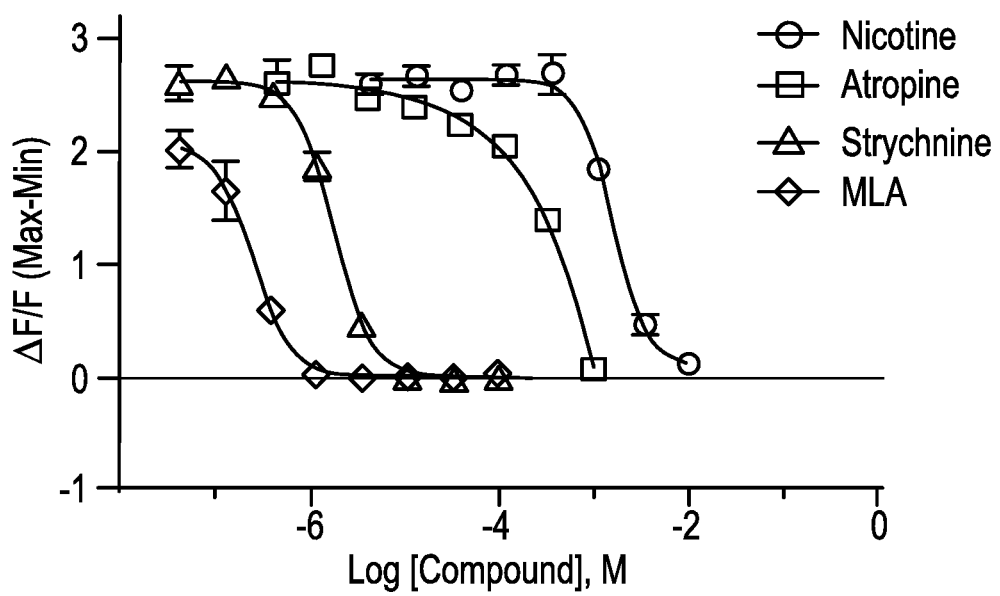

HEK293T cells were co-transfected as described in Example 1 with α9α10 nAChR and CHAT, α9α10 nAChR and TMIE, or α9α10 nAChR, CHAT and TMIE. After two days incubation, cells were washed three times with assay buffer (137 mM NaCl, 4 mM KCl, 2 mM CaCl2, 1 mM MgCl2, 5 mM glucose, 10 mM HEPES pH7.4) and loaded with Calcium5 dye and 1.25 mM probenecid for 1 hr at room temperature (RT). After three washes, the plates were placed in the FLIPR stage. After establishing baseline, responses were evoked with 200 µM ACh for 180 seconds in the presence of varying concentrations of α9α10 nAChR antagonists: nicotine, atropine, strychnine, or methyllycaconitine (MLA). Maximal FLIPR responses to ACh were plotted (FIGS. 3A-C). These dose response curves showed a rank order of potency MLA>strychnine>atropine>nicotine that is in line with α9α10 nAChR in hair cells and oocytes (Elgoyhen et al., 2001) (Table 4). This profile is unique to α9α10 nAChRs as opposed to any other known receptor (Elgoyhen et al., 2001).

TABLE 4

| | Antagonist $IC_{50}$ (µM) | | | |
|---|---|---|---|---|
| Gene Name | Nicotine | Atropine | Strychnine | MLA |
| α9α10 nAChR + CHAT | 384 | 12.3 | 1.3 | 0.16 |
| α9α10 nAChR + TMIE | 544 | 15.7 | 0.76 | 0.14 |
| α9α10 nAChR + CHAT + TMIE | 1500 | 340.3 | 1.8 | 0.26 |

Example 4. Effect of Preincubation with ACh or MLA on α9α10 nAChR Expression

Identification of CHAT, the biosynthetic enzyme for ACh, as a hit suggested that ACh itself may enable functional expression of α9α10 nAChR. To test this hypothesis, HEK293T cells were co-transfected as described in Example 1 with α9α10 nAChR and TMIE. Twenty-four hours after transfection, varying concentrations of either ACh or MLA were added to the wells and cells were incubated a further 24 hrs. Cells were washed three times with assay buffer (137 mM NaCl, 4 mM KCl, 2 mM CaCl2, 1 mM MgCl2, 5 mM glucose, 10 mM HEPES pH7.4) and loaded with Calcium5 dye and 1.25 mM probenecid for 1 hr at room temperature (RT). After three washes, the plates were placed in the FLIPR stage. FLIPR responses evoked by 200 µM ACh for 180 seconds were then recorded.

Figure 4:
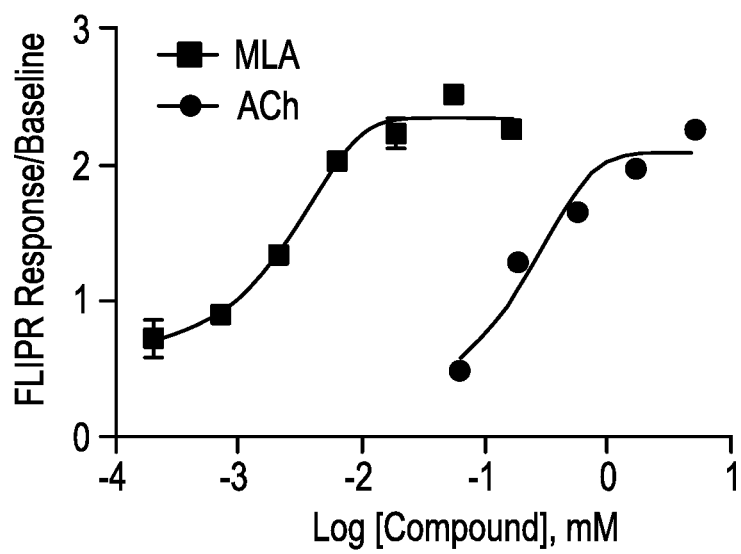
FIG. 4 shows a graph of FLIPR traces from HEK293T cells transfected with α9α10 and TMIE and incubated with varying concentrations of either acetylcholine (ACh) or methyllycaconitine (MLA). Responses were evoked by treating cells with 200 μM ACh for 180 seconds.

Preincubation for 24 hrs with either ACh or MLA enhanced ACh-evoked responses. MLA was more potent than ACh in this preincubation-mediated upregulation of α9α10 responses (FIG. 4).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

We claim:

1. An expression system for functional expression of α9α10 nAChR comprising a recombinant cell, wherein the recombinant cell is a cell transfected with one or more expression vectors, the one or more expression vectors comprising:
   (i) a first nucleic acid encoding an α9 subunit of an α9α10 nicotinic acetylcholine receptor (nAChR), wherein the α9 subunit of the α9α10 nAChR comprises an amino acid sequence with at least 95% identity to the amino acid sequence of SEQ ID NO:1;
   (ii) a second nucleic acid encoding an α10 subunit of an α9α10 nAChR, wherein the α10 subunit of the α9α10 nAChR comprises an amino acid sequence with at least 95% identity to the amino acid sequence of SEQ ID NO:2; and
   (iii) a third nucleic acid encoding Choline O-acetyltransferase (CHAT), wherein the CHAT comprises an amino acid sequence with at least 95% identity to the amino acid sequence of SEQ ID NO:3.

2. The expression system of claim 1, wherein the recombinant cell is a mammalian cell.

3. The expression system of claim 2, wherein the mammalian cell is selected from the group consisting of a human embryonic kidney 293T (HEK293T) cell, a HEK293F cell, a HeLa cell, a Chinese hamster ovary (CHO) cell, a NIH 3T3 cell, a MCF-7 cell, a Hep G2 cell, a baby hamster kidney (BHK) cell, and a Cos7 cell.

4. The expression system of claim 1, wherein the recombinant cell further comprises a fourth nucleic acid encoding at least one protein selected from the group consisting of TMIE, TMEM132A, TMEM132C, TMEM132D, TMEM132E, TMEM100 and TNFRSF10AU, wherein the TMIE comprises an amino acid sequence with at least 95% identity to the amino acid sequence of SEQ ID NO:4, wherein the TMEM132A comprises an amino acid sequence with at least 95% identity to the amino acid sequence of SEQ ID NO:5, the TMEM132C comprises an amino acid sequence with at least 95% identity to the amino acid sequence of SEQ ID NO:6, the TMEM132D comprises an amino acid sequence with at least 95% identity to the amino acid sequence of SEQ ID NO:7, the TMEM132E comprises an amino acid sequence with at least 95% identity to the amino acid sequence of SEQ ID NO:8, the TMEM100 comprises an amino acid sequence with at least 95% to the amino acid sequence of SEQ ID NO:9, and the TNFRSF10A comprises an amino acid sequence with at least 95% identity to the amino acid sequence of SEQ ID NO:10.

5. The expression system of claim 4, wherein the fourth nucleic acid encodes TMIE comprising an amino acid sequence with at least 95% identity to the amino acid sequence of SEQ ID NO:4.

6. A kit comprising (i) the expression system of claim 1; and (ii) instructions for use.

* * * * *